(12) United States Patent
Seldon et al.

(10) Patent No.: US 9,468,686 B2
(45) Date of Patent: Oct. 18, 2016

(54) SOLUTIONS COMPRISING POLYETHYLENE GLYCOL AND ELECTROLYTES

(71) Applicant: NORGINE BV, Amsterdam Zuid-Oost (NL)

(72) Inventors: Chris Seldon, London (GB); Dawn Padfield, London (GB); Frances Morrissey, London (GB)

(73) Assignee: NORGINE BV, Amsterdam Zuid-Oost (NL)

( * ) Notice: Subject to any disclaimer, the term of this patent is extended or adjusted under 35 U.S.C. 154(b) by 40 days.

(21) Appl. No.: 14/166,716

(22) Filed: Jan. 28, 2014

(65) Prior Publication Data

US 2014/0147518 A1    May 29, 2014

Related U.S. Application Data

(63) Continuation of application No. 13/387,791, filed as application No. PCT/GB2010/001455 on Jul. 30, 2010, now abandoned.

(30) Foreign Application Priority Data

Jul. 30, 2009   (GB) .................................. 0913295.2

(51) Int. Cl.
| | |
|---|---|
| A61K 47/14 | (2006.01) |
| A61K 31/08 | (2006.01) |
| A61K 47/10 | (2006.01) |
| A61K 33/14 | (2006.01) |
| A61K 9/00  | (2006.01) |

(52) U.S. Cl.
CPC ............ *A61K 47/14* (2013.01); *A61K 9/0095* (2013.01); *A61K 31/08* (2013.01); *A61K 33/14* (2013.01); *A61K 47/10* (2013.01)

(58) Field of Classification Search
CPC .... A61K 9/0095; A61K 47/10; A61K 33/14; A61K 47/14
See application file for complete search history.

(56) References Cited

U.S. PATENT DOCUMENTS

| | | | |
|---|---|---|---|
| 5,378,470 A | 1/1995 | Lahr | |
| 5,710,183 A | 1/1998 | Halow | |
| 7,291,324 B2 | 11/2007 | Dennett, Jr. et al. | |
| 2004/0192614 A1 | 9/2004 | Vanner et al. | |
| 2005/0003021 A1 | 1/2005 | Sugiyama et al. | |
| 2006/0029570 A1 | 2/2006 | Aronson et al. | |
| 2007/0082061 A1 | 4/2007 | Ayala et al. | |
| 2008/0260682 A1 | 10/2008 | Rose et al. | |
| 2009/0182052 A1 | 7/2009 | Djordjevic et al. | |

FOREIGN PATENT DOCUMENTS

| | | |
|---|---|---|
| DE | 102006001199 A1 | 7/2007 |
| EP | 1048297 A2 | 11/2000 |
| JP | H1-132527 | 5/1989 |
| RU | 2111741 C1 | 10/1994 |
| TW | 200930385 | 7/2009 |
| WO | WO 87/00754 A1 | 2/1987 |
| WO | WO 94/12191 A1 | 6/1994 |
| WO | WO 98/43654 A1 | 10/1998 |
| WO | WO 99/62498 A1 | 12/1999 |
| WO | WO 02/03973 A2 | 1/2002 |
| WO | WO 03/092589 A2 | 11/2003 |
| WO | WO 2004/037292 A1 | 5/2004 |
| WO | WO 2005/007170 A1 | 1/2005 |
| WO | WO 2005/049049 A1 | 6/2005 |
| WO | WO 2005/102364 A1 | 11/2005 |
| WO | WO 2006/122104 A1 | 11/2006 |
| WO | WO 2007/085676 A1 | 8/2007 |
| WO | WO 2009/036906 A1 | 3/2009 |

OTHER PUBLICATIONS

ISCA, "News", accessed at https://web.archive.org/web/20101206184639/http://www.iscauk.com/content/news.htm on Jun. 17, 2016.*
ISCA, "Iscaguard Preservatives for Personal Care", accessed at http://www.iscauk.com/downloads/Iscaguard_Preservatives_for_Personal_Care.pdf on Jun. 17, 2016.*
TRILYTE Drug Label, Alaven Pharmaceutical LLC, (2008), permanent link: http://dailymed.nlm.nih.gov/dailymed/drugInfo.cfm?setid=7cc71392-22b1-4234-a0e2-e227824409de (revised Aug. 2009).
DiPalma et al., Gastrointestinal Endoscopy, 36(3): 285-289 (1990).
Beringer et al., Remington: The Science and Practice of Pharmacy, 21st Ed., Lippincott Williams & Wilkins (2005), pp. 747-749.
Applicant's Response dated Apr. 15, 2011 to the Combined Search and Examination Report under Sections 17 and 18 (3) of Nov. 4, 2010.
Applicant's Response dated Dec. 14, 2011 to the Combined Search and Examination Report under Sections 17 and 18(3) of Jun. 15, 2010.
GB Combined Search and Examination Report on priority application GB0913295.2 (Nov. 30, 2009).

(Continued)

*Primary Examiner* — Kortney L Klinkel
*Assistant Examiner* — Lisbeth C Robinson
(74) *Attorney, Agent, or Firm* — Yankwich & Associates, P.C.; Leon R. Yankwich; Michael R. Wesolowski

(57) ABSTRACT

A solution in water comprising the following components at the following concentrations: (a) N×(70 to 130) g/L polyethylene glycol (PEG) having an average molecular weight of 2500 to 4500; (b) N×(1.6 to 4.0) g/L sodium chloride; (c) N×(0.2 to 0.6) g/L potassium chloride; (d) N×(0.6 to 2.2) g/L sodium bicarbonate; (e) N×an amount of preservative; (f) optionally N x an amount of flavouring; and (g) optionally N×an amount of sweetener, where N is in the range of 2 to 8. The solution is a concentrate for dilution. In use it is diluted N-fold with water to provide a solution for administration to a subject for the treatment of constipation or faecal impaction. Also provided are solutions, kits, unit doses and methods that comprise or use the solutions.

27 Claims, No Drawings

(56) References Cited

OTHER PUBLICATIONS

GB Combined Search and Examination Report on GB equivalent application GB1012903.9 (Nov. 4, 2010).
GB Combined Search and Examination Report on GB equivalent application GB1108383.9 (Jun. 14, 2011).
International Search Report (ISR) and Written Opinion of the International Searching Authority for international application No. PCT/GB2010/001455 (Oct. 12, 2010).
International Search Report (ISR) and Written Opinion of the International Searching Authority for international application No. PCT/GB2012/050195 (Apr. 18, 2012).
NL Search Report and Written Opinion issued on NL equivalent application NL2005176.
Cleland et al., "Tracer Experiments on the Mechanism of Citric Acid Formation by Aspergillus Niger", J. Biol. Chem., 208: 679-690 (1954).
Colace Stool Softener Syrup Information Sheet (2009).
Colace Stool Softener Liquid 1% Solution Information Sheet (2009).
eMC entry for Movical 13.8g sachet, powder for oral solution (Mar. 2007).
NuLYTELY Information Sheet (Mar. 2008).
Wallin et al., "Release of Somatostatin, Neurotensin and Vasoactive Intestinal Peptide Upon Inhibition of Gastric Acid Secretion by Duodenal Acid and Hyperosmolal Solutions in the Conscious Rat", Acta Physiol. Scand., 154: 193-203 (1995).
Iscaguard MEB Material Safety Data Sheet (MSDS)(Oct. 27, 2008).
Iscaguard MEB sales specification (Oct. 28, 2008).
Wu et al., "Reactive Impurities in Excipients: Profiling, Identification and Mitigation of Drug-Excipient Incompatibility", AAPS PharmSciTech, 12(4): 1248-1263 (Sep. 2011).
Handbook of Pharmaceutical Excipients, Eds. Rowe, Sheskey, Owen, Fifth Edition, Pharmaceutical Press and American Pharmacists Association (London, UK; Washington DC) (2006).
Handbook of Pharmaceutical Excipients, Rowe, Raymond C Editor, Pharmaceutical Press, London, Fifth Edition, pp. 545-550 (2006).

* cited by examiner

SOLUTIONS COMPRISING POLYETHYLENE GLYCOL AND ELECTROLYTES

CROSS-REFERENCE TO RELATED APPLICATIONS

This application is a continuation of pending U.S. application Ser. No. 13/387,791, filed Jan. 30, 2012, which is a United States national stage filing under 35 U.S.C. §371 of international (PCT) application no. PCT/GB2010/001455, filed Jul. 30, 2010, and designating the US, which claims priority to GB application no. 0913295.2, filed Jul. 30, 2009.

The present invention relates to solutions for the treatment of constipation or faecal impaction. In particular it relates to concentrates for use in the preparation of solutions comprising polyethylene glycol (PEG) and electrolytes.

Constipation is a widespread condition which generally gives rise to discomfort. The physical presence of faeces retained in the colon and/or the rectum gives rise to a feeling of malaise and headaches. In extreme cases of prolonged constipation, dyschezia may result from the presence of scybala or faecaliths in the rectum.

Numerous treatments of constipation have been developed, including dietary manipulation (e.g. increasing the fibre content of the diet and removing foods considered to be constipation causing), laxatives and enemas. Laxatives are agents that promote and assist defecation. Osmotic laxatives act to retain water in the colonic lumen thereby counteracting the normal dehydrating action of the colon. By suppressing the dehydration action of the colon, the osmotic laxative produces a faecal stream which is softer, bulkier and easier to expel.

A number of osmotic laxative treatments currently in use comprise polyethylene glycol (PEG) and electrolytes. Various such PEG/electrolyte products are on the market in many countries. An example of such a product is MOVICOL (registered trademark of Edra AG, exclusively licensed to the Norgine group of companies, and marketed in the UK by Norgine Limited, Chaplin House, Widewater Place, Moorhall Road, Harefield, Uxbridge, Middlesex UB9 6NS, United Kingdom). MOVICOL is provided in a sachet containing 13.8 g powder for making up into an oral solution. Each sachet contains: 13.1250 g Macrogol (polyethylene glycol (PEG)) 3350, 0.3507 g sodium chloride, 0.1785 g sodium bicarbonate and 0.0466 g potassium chloride. This is the standard dose of MOVICOL. It also contains flavouring and sweetener. MOVICOL has been on the market since 1995. MOVICOL PLAIN is essentially the same as MOVICOL but it does not contain flavouring or sweetener, so to adjust for the potassium content of the sweetener, it contains slightly more potassium chloride. Each sachet of MOVICOL PLAIN contains: 13.1250 g Macrogol (polyethylene glycol (PEG)) 3350, 0.3508 g sodium chloride, 0.1786 g sodium bicarbonate and 0.0502 g potassium chloride. When MOVICOL or MOVICOL PLAIN is made into a drink with water to a volume of 125 milliliters, each sachet gives the equivalent of: 65 millimoles/liter sodium, 53 millimoles/liter chloride, 17 millimoles/liter bicarbonate and 5.4 millimoles/liter potassium.

One standard dose of MOVICOL is provided as a unit treatment in powder form in one sachet. Patients are advised to combine the powder contents of a sachet with water to make up a drink of 125 ml. It is found that dissolution can, in practice, take some time. It is important with a solution of the MOVICOL type that the patient does not to attempt to speed the dissolution by heating as that will lead to decomposition of the bicarbonate component. The time taken for the powder to dissolve causes inefficiency in the care-home or hospital setting where solutions are prepared by professional care-providers. In the self-administration domestic setting, it can cause frustration in the patient and risks the patient taking an incompletely dissolved preparation, which would reduce the efficacy of the treatment. The sachets are made of a laminate consisting of four layers: low density polyethylene, aluminium, low density polyethylene and paper. Some patients have difficulties manipulating and tearing open the sachets. The sachets are not re-usable.

For the treatment of constipation, patients are advised to take one sachet dissolved to 125 ml 1-3 times a day, according to the severity of the constipation. Treatment with MOVICOL usually lasts about 2 weeks. There are various situations in which MOVICOL is recommended for longer treatments than 2 weeks, particularly in patients who take drugs that cause constipation (eg opioids, such as morphine) or have a disease that has associated constipation (for example Parkinson's disease or multiple sclerosis (MS)). Usually, for long term treatment in such chronic treatment situations, the number of doses per day can be adjusted down to either one or two.

For the treatment of faecal impaction, the recommended treatment is 8 sachets a day (each dissolved to 125 ml), taken within 6 hours. That number of doses may be needed for up to 3 days.

MOVICOL sachets can be provided in boxes of 2, 6, 8, 10, 20, 30, 50, 60 or 100 sachets. Not all pack size boxes are necessarily marketed at any one time. Examples of marketed boxes are those containing 6, 30 or 100 sachets in the box (ie 6, 30 or 100 standard doses). Those boxes have the following dimensions:

6 pack:
  Has dimensions 14.5 cm×3.7 cm×13.0 cm, giving a volume of 697.45 cm$^3$ per pack, ie 116.24 cm$^3$ per standard dose.

30 pack:
  Has dimensions 14.5 cm×9.0 cm×13.0 cm, giving a volume of 1696.50 cm$^3$ per pack, ie 56.55 cm$^3$ per standard dose.

100 pack:
  Has dimensions 29.0 cm×14.5 cm×12.5 cm, giving a volume of 5256.25 cm$^3$ per pack, ie 52.56 cm$^3$ per standard dose.

Each sachet measures roughly 12 cm by 7 cm and is flat, bulging to around 1 cm thickness when full.

Since many patients take MOVICOL or similar constipation-treatment solutions chronically (ie for extended periods), it is common for it to be necessary to store these large multi-pack boxes either in a patient's home or in a care-home or hospital drug storage cupboard. In a patient's home or in a care-home or hospital, medicinal products must be stored carefully and safely, and medicinal product storage space is generally at a premium. The large amount of space taken up by the necessary multi-pack boxes can be costly and cause difficulties.

Concentrated solutions of some pharmaceuticals for dilution are known, and a small number are on the market. Despite there being scope for practical improvements in use for the powder PEG/electrolye compositions on the market, no concentrated solutions of PEG/electrolyes for dilution to PEG-containing laxatives have been developed to commercialisation. Concentrated solutions of PEG/sodium sulphate lavage solutions have been proposed (see WO 2005/049049 and JP H1-132527), but no such solutions have been commercialised. In WO2005/049049 it was disclosed that "concentrated solutions of polyethylene glycol are chemically stable and do not support microbial growth" and thus do not need preservatives. In JP H1-132527, data are presented showing that in solutions of 118 g/L PEG 4000, 11.4 g/L sodium sulphate, 1.48 g/L potassium sulphate, 2.93 g/L sodium chloride and 3.37 g/L sodium bicarbonate, and solutions with 1.5, 2 and 2.5 times those concentrations, "there was no propagation of the micro-organisms at all". It was thus disclosed that "no sterilization or added preservatives" were needed. However, and in contrast to those publications, the current inventors have found that a concentrated solution of PEG, sodium chloride, potassium chloride and sodium bicarbonate (and no sodium sulphate), supports microbial growth to an unacceptable extent.

It has been found by the present inventors that a preservative is essential in solutions comprising N×(70 to 130) g/L PEG having an average molecular weight of 2500 to 4500, (b) N×(1.6 to 4.0) g/L sodium chloride, (c) N×(0.2 to 0.6) g/L potassium chloride, and (d) N×(0.6 to 2.2) g/L sodium bicarbonate (and no sodium sulphate), where N is in the range 2 to 8, for example in solutions comprising 350 to 600 g/L PEG having an average molecular weight of 2500 to 4500, 8.0 to 20 g/L sodium chloride, 1.0 to 3.0 g/L potassium chloride and 3.0 to 11 g/L sodium bicarbonate (and no sodium sulphate). Inclusion of a suitable amount of a suitable preservative in such a solution allows microbial growth to be limited or eliminated.

Accordingly, in order to overcome the above-mentioned difficulties, there is provided a solution in water comprising the following components at the following concentrations:
  (a) N×(70 to 130) g/L PEG having an average molecular weight of 2500 to 4500;
  (b) N×(1.6 to 4.0) g/L sodium chloride;
  (c) N×(0.2 to 0.6) g/L potassium chloride;
  (d) N×(0.6 to 2.2) g/L sodium bicarbonate;
  (e) N×an amount of preservative;
  (f) optionally N×an amount of flavouring; and
  (g) optionally N×an amount of sweetener
  where N is a number in the range of 2 to 8.

The solution is a concentrate for N-fold dilution with water to provide a solution for ingestion comprising the following components at the following concentrations:
  (a) 70 to 130 g/L PEG having an average molecular weight of 2500 to 4500;
  (b) 1.6 to 4.0 g/L sodium chloride;
  (c) 0.2 to 0.6 g/L potassium chloride;
  (d) 0.6 to 2.2 g/L sodium bicarbonate;
  (e) an amount of preservative;
  (f) optionally an amount of flavouring; and
  (g) optionally an amount of sweetener.

The concentrate solution is preferably accompanied by instructions instructing the user to dilute with water by N-fold. N need not be an integer, but it is the same number for each component. Dilution of a solution of volume V by N-fold requires the addition of a volume (N−1)×V of water. Preferably N is from 3 to 7, for example from 4 to 6, for example 5.

Preferably, the amount of PEG is N×(70 to 120) g/L, more preferably N×(80 to 120) g/L, more preferably N×(95 to 115) g/L, for example N×105 g/L. Preferably, the amount of sodium chloride N×(2.1 to 3.5) g/L, more preferably N×(2.4 to 3.2) g/L, more preferably N×(2.6 to 3.0) g/L, for example approximately N×2.8 g, for example N×2.8056 g/L. Preferably, the amount of potassium chloride is N×(0.28 to 0.45) g/L, more preferably N×(0.32 to 0.42) g/L, more preferably N×(0.35 to 0.40) g/L, for example approximately N×0.37 g/L, for example N×0.3728 g/L. Preferably, the amount of sodium bicarbonate is N×(1.1 to 1.7) g/L, more preferably N×(1.2 to 1.6) g/L, more preferably N×(1.35 to 1.50) g/L, for example approximately N×1.4 g/L, for example N×1.428 g/L.

For example, the invention provides a concentrate solution in water comprising the following components at the following concentrations:
  (a) 350 to 600 g/L PEG having an average molecular weight of 2500 to 4500;
  (b) 8.0 to 20 g/L sodium chloride;
  (c) 1.0 to 3.0 g/L potassium chloride;
  (d) 3.0 to 11 g/L sodium bicarbonate;
  (e) preservative;
  (f) optional flavouring; and
  (g) optional sweetener.

Solutions of the invention are preferably substantially free from any sulphate component. In particular, solutions of the invention are preferably substantially free from sodium sulphate. In this context, "substantially free from any sulphate component" is taken to mean free from any added sulphate component. Negligible amounts of sulphate salts may be present in other added components, or in the water that is used in the solutions. Such amounts are not substantial in this context.

In use, the solution of the invention is diluted with additional water to provide a medicament for drinking by a patient. The solution of the invention can thus be regarded as a concentrate. In use, a solution of the invention is, for example, diluted with approximately four times its volume of water to generate an approximately five-fold diluted solution. For example, a 25 ml unit of the concentrate solution may be diluted with from 75 to 125 ml of water to give a solution of from 100 ml to 150 ml.

A "solution" in the context of the present invention includes any mixture resulting from admixture of or combination of the components (a) to (g) with water, whether fully dissolved or not. In a preferred embodiments, the components (a) to (g) are fully dissolved.

Solutions of the invention have been found to be particularly convenient for use in providing one or more of the following advantages:
  1. They can be made up to the medicament solution for drinking in less time than the dry powder compositions of the prior art.
  2. They enable storage of the medicament in a smaller volume than for sachets of dry powder of the prior art.
  3. They have a shelf life sufficiently long to be acceptable in a pharmaceutical product.

These are expanded on below:
1. It has been found that the solutions of the invention can be diluted to the concentration required for ingestion more rapidly than the dry powders of the prior art. The solution at the concentration for ingestion is prepared essentially instantly once the concentrate solution of the invention is mixed with the diluting water. There is no delay for the dissolution of dry powder. The rapid preparation of the solution for ingestion reduces the time taken to prepare the medicament. That reduction in time brings about improved efficiency in the care-home or hospital setting where solutions are prepared by professional care-providers. In the self-administration, domestic setting, it reduces the risk of patient frustration and improves patient compliance.
2. A unit treatment may be provided in a unit container. Suitable containers include bottles, pouches, vials or sealed cups. Such containers suitably have the volume required to accommodate the unit treatment. Preferably, they do not include air-pockets or significant wasted space. In that way, storage space is minimized. Provided the unit containers are appropriately shaped for efficient packing (eg cylindrical, cuboid or hexagonal, though many other shapes are possible), and provided wasted volume is minimised, a unit treatment can be stored in a volume only little greater than its own volume. Thus, when a solution of the invention comprises 525 g of PEG 3350 per liter and N is 5, then 25 ml of that is required to provide the 13.125 g of PEG in a standard dose and, in storage, that will occupy (with its container) only slightly more than 25 cm$^3$, for example 30 cm$^3$. That represents a space saving of around 20 cm$^3$ compared with the over 50 cm$^3$ storage space required per unit treatment (ie per standard dose) mentioned above in relation to sachets of dry powder comprising the same quantity of ingredients.

The solution of the invention may be provided in a container having a volume that is for multiple unit treatments. The invention thus further provides a container that contains sufficient solution for any convenient number of unit treatments. For example, the container might provide 1, 2, 4, 5, 8, 10, 12, 15, 20, 25, 30, 35, 40, 50, 60, 70, 75, 80 or 100 unit treatments. For example, if a solution of the invention comprises 525 g of PEG 3350 per liter, and 25 ml are required to provide the 13.125 g of PEG in a standard dose, then a container may provide 25 ml, 50 ml, 100 ml, 125 ml, 150 ml, 200 ml, 250 ml, 300 ml, 375 ml, 500 ml, 625 ml, 750 ml, 875 ml or 1l of solution. For example a container may contain one or more unit treatments of solution, each unit treatment having a volume of 20 to 50 ml, for example 25 ml, or each unit treatment having a volume of 7.5 to 25 ml, for example 12.5 ml. For example, a container (for example a bottle) of the invention provides 100 ml, 150 ml, 250 ml or 500 ml of solution of the invention.

Suitable containers include bottles, for example with a re-closable closure. A re-closable closure may be child-proof. A re-closable closure may be tamper-evident. Containers may for example be made of plastic or glass, for example polyethylene terephthalate (PET). They may be circular in cross-section, for example they may be a right circular cylinder. They may be transparent, translucent or opaque; containers may be coloured, for example amber.

Considering again a 25 ml unit treatment that provides the 13.125 g of PEG in a standard dose, then 20 unit treatments are provided in a container of 500 ml volume. The container can be designed with a shape that takes up minimal unnecessary space and thus the 20 unit treatments may be stored in a volume of only a little over 500 cm$^3$. That is to say that they occupy only slightly over 25 cm$^3$ each. That represents a space saving of around 20 cm$^3$ compared with the over 50 cm$^3$ storage space required per standard dose mentioned above in relation to sachets of dry powder comprising the same quantity of ingredients.

In addition, a container containing multiple unit treatments has further practical and environmental advantages in that it is easier to use and generates less waste than multiple sachets. Such a container can potentially be re-used or recycled, something that is not possible with sachets.

3. As mentioned above, in contrast to the published art, it has been found by the present inventors that, in solutions comprising N×(70 to 130) g/L PEG having an average molecular weight of 2500 to 4500, (b) N×(1.6 to 4.0) g/L sodium chloride, (c) N×(0.2 to 0.6) g/L potassium chloride, and (d) N×(0.6 to 2.2) g/L sodium bicarbonate (and no sodium sulphate), when N is in the range 2 to 8, for example 350 to 600 g/L PEG having an average molecular weight of 2500 to 4500, 8.0 to 20 g/L sodium chloride, 1.0 to 3.0 g/L potassium chloride and 3.0 to 11 g/L sodium bicarbonate (and no sodium sulphate), a preservative is essential. Inclusion of a suitable amount of a suitable preservative in such a solution allows microbial growth to be limited or eliminated, and thus acceptable shelf or storage life to be achieved.

Various national and regional pharmacopoeias set criteria that oral preparations must fulfil regarding their propensity to support micro-organism growth. For example, in order to meet the criteria of the European Pharmacopoeia for an oral preparation, a solution must satisfy the following: 3 log units drop in number of viable micro-organisms for bacteria over 14 days (typically assessed using *Pseudomonas aeruginosa, Escherichia coli* and *Staphylococcus aureus*, the drop being required for each), and 1 log unit drop for yeasts and moulds over 14 days (typically assessed using *Candida albicans* and *Aspergilus niger*). Also, for bacteria and yeasts/moulds, there must then be no increase from 14 days to 28 days. It has been found that, in a solution comprising N×(70 to 130) g/L PEG having an average molecular weight of 2500 to 4500, (b) N×(1.6 to 4.0) g/L sodium chloride, (c) N×(0.2 to 0.6) g/L potassium chloride, and (d) N×(0.6 to 2.2) g/L sodium bicarbonate (and no sodium sulphate), where N is in the range 2 to 8, for example a solution comprising 350 to 600 g/L PEG having an average molecular weight of 2500 to 4500, 8.0 to 20 g/L sodium chloride, 1.0 to 3.0 g/L potassium chloride and 3.0 to 11 g/L sodium bicarbonate (and no sodium sulphate), yeast and mould growth containment do not meet these criteria if no effective preservative is included.

Various preservatives are known for use in liquid oral preparations. Examples of such preservatives include sodium propyl paraben, methyl paraben, ethyl paraben, propyl paraben, benzyl alcohol and phenoxyethanol. Further preservatives that are known for use in liquid oral preparations (including foods) include benzoic acid, dehydroacetic acid, sorbic acid, Bronopol, propylene glycol and glyceryl triacetate. Alcohols are used as preservatives in some preparations.

The preservative component may comprise one, two or more preservatives. The preservative may be (i) a separate component from the other components of the solution and mixed therewith, (ii) a constituent part of a flavouring component (f), sweetener component (g) or other component of a solution of the invention, or (iii) both (i) and (ii).

Particularly preferred preservatives are those that are active and/or do not degrade over time at alkaline pH. Preferred preservatives include sodium propyl paraben, methyl paraben, ethyl paraben, propyl paraben, benzyl alcohol, phenoxyethanol, propylene glycol, glyceryl triacetate and blends of two or more of those. Methyl paraben, ethyl paraben, propyl paraben, benzyl alcohol and phenoxyethanol and blends of two or more of those are particularly preferred. Appropriate preservatives may be provided as salts, for example sodium salts. In solutions of the invention, a preservative is preferably not provided as a salt; if a preservative is provided as a salt, then the electrolyte components (b) to (d) may need to be adjusted so that the total concentration of each electrolyte remains at the required level. For example, if a preservative is used in the form of a sodium salt, it may be necessary to reduce the amount of sodium chloride present.

It is important that the level of preservative in any oral formulation does not exceed recommended safe levels for oral use. For an oral preparation that will be given to a patient several times per day, it is important that the cumulative level of preservative is sufficiently low not to exceed recommended daily intake levels. Preferred preservatives have ADI (acceptable daily intake) levels that have been confirmed by suitable regulatory bodies, for example the EFSA. Methyl paraben, ethyl paraben, benzyl alcohol and blends of two or more of those are particularly preferred.

For the solutions of the present invention, it has been found that the preservative may be present at a level of from 0.5 to 10 g per liter of solution (ie 0.05 to 1 w/v %), for example 1.5 to 7.0 g per liter of solution (ie 0.15 to 0.7 w/v %). For example, a preservative may be present at a level of from 1.0 to 5.0 g per liter of solution (ie 0.1 to 0.5 w/v %), for example 2.0 to 4.0 g per liter of solution (ie 0.2 to 0.4 w/v %). For example, a preservative may be present at a level of from N×(0.1 to 2.0) g per liter of solution, for example from N×(0.3 to 1.4) g per liter of solution, for example from N×(0.2 to 1.0) g per liter of solution, for example N×(0.4 to 0.8) g per liter of solution.

Certain preservatives have limited solubility in water. The effectiveness of a preservative can be improved by the inclusion of a solubilising agent. Examples of solubilising agents include benzyl alcohol, phenoxyethanol and propylene glycol. A solubilising agent may be (i) a separate component from the other components of the solution and mixed therewith, (ii) a constituent part of a preservative component (e), a flavouring component (f), sweetener component (g) or other component of a solution of the invention, or (iii) both (i) and (ii). It is important that the level of a solubilising agent in any oral formulation does not exceed recommended safe levels.

In a preferred embodiment, a preservative comprises 20-30% by weight (relative to the weight of the preservative) paraben (which may be a single paraben or a mixture of parabens), and 70-80% by weight solubiliser. It is thus preferred that, in one embodiment, a solution of the invention includes one or both of methyl paraben and ethyl paraben, and benzyl alcohol. In an embodiment, a solution of the invention includes one or both of methyl paraben and ethyl paraben, and phenoxyethanol.

Therefore, suitable preservatives should fulfil multiple criteria: they should be active and/or not degrade over time at alkaline pH, and be sufficiently effective to fulfill national and regional pharmacopoeial criteria regarding micro-organism growth when used in an amount that is safe for human consumption.

It has been found that a blend of methyl paraben, ethyl paraben and benzyl alcohol is particularly effective as a preservative component in a solution of the invention (not containing sodium sulphate), and that effective anti-microbial preservation is achieved with a particularly low level of preservative. Preferably, a solution of the invention includes all three of methyl paraben, ethyl paraben and benzyl alcohol. For example, they may be present in a weight ratio methyl paraben:ethyl paraben:benzyl alcohol of 1 to 3:1:5 to 12, for example 1.5 to 2.5:1:7 to 9. For example, in the ratio 18:9:73. It has been found that a blend of methyl paraben, ethyl paraben and benzyl alcohol is particularly effective in preventing the growth of *Aspergilus niger*. That mould can be particularly challenging in solutions of high osmolality, for example concentrate solutions such as those of the invention.

Preferably, a blend of methyl paraben, ethyl paraben and benzyl alcohol is present at a level of from N×(0.3 to 1.4) g per liter of solution, preferably from 1.5 to 7.0 g per liter of solution (ie 0.15 to 0.70 w/v %), preferably from 2.0 to 7.0 g per liter of solution (ie 0.20 to 0.70 w/v %), for example (particularly when the solution comprises an Orange Juice flavour) from 2.5 to 7.0 g per liter of solution (ie 0.25 to 0.7 w/v %), for example 2.5 to 5.0 g per liter of solution (ie 0.25 to 0.5 w/v %). A preferred solution comprises 2.5 g or 3.5 g of a blend of methyl paraben, ethyl paraben and benzyl alcohol per liter, for example 2.5 or 3.5 g per liter of a blend of methyl paraben (18%), ethyl paraben (9%) and benzyl alcohol (73%), the weight % being based on the weight of the preservative component.

Accordingly, a preferred concentrate solution of the invention comprises:
(a) N×(70 to 130) g/L PEG having an average molecular weight of 2500 to 4500;
(b) N×(1.6 to 4.0) g/L sodium chloride;
(c) N×(0.2 to 0.6) g/L potassium chloride;
(d) N×(0.6 to 2.2) g/L sodium bicarbonate;
(e) N×(0.3 to 1.4) g/L of preservative comprising methyl paraben, ethyl paraben or benzyl alcohol, or a mixture of two or more of them;
(f) optionally N x an amount of flavouring; and
(g) optionally N x an amount of sweetener
where N is in the range of 2 to 8.

For example, a preferred concentrate solution of the invention comprises the following components at the following concentrations:
(a) 350 to 600 g/L PEG having an average molecular weight of 2500 to 4500;
(b) 8.0 to 20 g/L sodium chloride;
(c) 1.0 to 3.0 g/L potassium chloride;
(d) 3.0 to 11 g/L sodium bicarbonate;
(e) 1.5 to 7.0 g/L of preservative comprising methyl paraben, ethyl paraben or benzyl alcohol, or a mixture of two or more of them;
(f) optional flavouring; and
(g) optional sweetener.

It has also been found that blends of methyl paraben, ethyl paraben and phenoxyethanol have good effectiveness as a preservative in a solution of the invention (not containing sodium sulphate). For example, a solution of the invention includes all three of methyl paraben, ethyl paraben and phenoxyethanol. For example, they may be present in a weight ratio methyl paraben:ethyl paraben:phenoxyethanol of 1 to 3:1:5 to 12, for example 1.2 to 2.5:1:7 to 9. For example, in the ratio 18:9:73, or 15:10:75.

A blend of methyl paraben, ethyl paraben and phenoxyethanol may be present at a level of from N×(1.0 to 2.0 g) per liter of solution, preferably from 5.0 to 10 g per liter of solution (ie 0.5 to 1.0 w/v %), for example 5.0 to 8.0 g per liter of solution (ie 0.5 to 0.8 w/v %). For example, a solution comprises 5.0 g of a blend of methyl paraben, ethyl paraben and phenoxyethanol per liter, for example 5.0 g per liter of a blend of methyl paraben (18%), ethyl paraben (9%) and phenoxyethanol (73%), the weight % being based on the weight of the preservative component.

In a further embodiment, a concentrate solution of the invention comprises:
(a) N×(70 to 130) g/L PEG having an average molecular weight of 2500 to 4500;
(b) N×(1.6 to 4.0) g/L sodium chloride;
(c) N×(0.2 to 0.6) g/L potassium chloride;
(d) N×(0.6 to 2.2) g/L sodium bicarbonate;
(e) N×(2.0 to 2.0) g/L of preservative comprising methyl paraben, ethyl paraben or phenoxyethanol, or a mixture of two or more of them;
(f) optionally N x an amount of flavouring; and
(g) optionally N x an amount of sweetener
where N is in the range of 2 to 8.

For example, a concentrate solution in water comprising the following components at the following concentrations:
(a) 350 to 600 g/L PEG having an average molecular weight of 2500 to 4500;
(b) 8.0 to 20 g/L sodium chloride;
(c) 1.0 to 3.0 g/L potassium chloride;
(d) 3.0 to 11 g/L sodium bicarbonate;
(e) 5.0 to 10.0 g/L of preservative comprising methyl paraben, ethyl paraben or phenoxyethanol, or a mixture of two or more of them;
(f) optional flavouring; and
(g) optional sweetener.

The polyethylene glycol (PEG) used in solutions of the invention has an average molecular weight (for example a weight average molecular weight), of 2500 Da to 4500 Da. The PEG may have an average molecular weight of 3000 to 4000. For example, the PEG may be PEG 3350 or PEG 4000 as defined in national pharmacopoeias. Further examples of suitable PEGs recognized in some national pharmacopoeias include Macrogols, for example Macrogol 4000. Optionally, the PEG used in compositions of the invention may comprise two or more different PEG compounds.

Depending on the molecular weight of the PEG in a solution of the invention, the upper limit of concentration of the PEG may be limited by the water solubility of the PEG. For certain values of N, it necessary for the (70 to 130) g factor in the N×(70 to 130) g/L amount to be nearer the lower end of the (70 to 130) g range for reasons of solubility. Solutions of the invention therefore preferably comprise PEG in an amount of 350 to 600 g per liter, preferably within a range wherein the lower limit is 400, 450 or 500 g per liter and the upper limit is, independently, 600, 575 or 550 g per liter; for example 500 to 550 g per liter. For example a solution of the invention may comprise 525 g of PEG per liter, for example 525 g of PEG 3350 per liter.

Solutions of the invention preferably comprise sodium chloride in an amount of 8.0 to 20 g per liter of solution to be made, preferably within a range wherein the lower limit is 10, 11, 12 or 13 g per liter and the upper limit is, independently, 18, 17, 16 or 15 g per liter; for example 13 to 15 g per liter. For example a solution of the invention may comprise approximately 14 g of sodium chloride per liter, for example 14.028 g per liter.

Solutions of the invention preferably comprise potassium chloride in an amount of 1.0 to 3.0 g per liter, preferably within a range wherein the lower limit is 1.2, 1.4, 1.6, 1.7 or 1.8 g per liter and the upper limit is, independently, 2.7, 2.5, 2.3, 2.1 or 2.0 g per liter; for example 1.6 to 2.1 g per liter, for example 1.8 to 1.9 g per liter. For example a solution of the invention may comprise 1.864 g of potassium chloride per liter. An alternative solution of the invention may comprise 1.268 g or 2.008 g of potassium chloride per liter. In an embodiment, the potassium ion content may be provided by a potassium salt other than potassium chloride.

Solutions of the invention preferably comprise sodium bicarbonate (also known as sodium hydrogen carbonate) in an amount of 3.0 to 11 g per liter, preferably within a range wherein the lower limit is 5.0, 6.0, 6.5 or 7.0 g per liter and the upper limit is, independently, 10, 9.0, 8.0 or 7.5 g per liter; for example 6.5 to 8.0 g per liter. For example a solution of the invention may comprise approximately 7.1 g per liter, for example 7.140 g per liter.

In a solution of the invention, the weight ratio of the components PEG, sodium chloride, potassium chloride and sodium bicarbonate is preferably approximately 13.125 (PEG):0.3507 (NaCl):0.0466 (KCl):0.1785 (NaHCO$_3$), ie approximately 282 (PEG):7.5 (NaCl):1 (KCl):3.8 (NaHCO$_3$). For example it may be within the ranges 250 to 450 (PEG):5 to 15 (NaCl):1 (KCl):3 to 7.5 (NaHCO$_3$), for example 250 to 300 (PEG):5 to 10 (NaCl):1 (KCl):3 to 5 (NaHCO$_3$), for example within the ranges 275 to 285 (PEG):7 to 8 (NaCl):1 (KCl):3.6 to 4.0 (NaHCO$_3$).

In another embodiment of a solution of the invention, the molar ratio of the individual ions in the components sodium chloride, potassium chloride and sodium bicarbonate is preferably approximately 65 (Na$^+$):53 (Cl$^-$):5.0 (K$^+$):17 (HCO$_3^-$), ie approximately 13 (Na$^+$):10.6 (Cl$^-$):1 (K$^+$):3.4 (HCO$_3^-$), For example it may be within the ranges 11 to 15 (Na$^+$):8 to 13 (Cl$^-$):1 (K$^+$):2.8 to 4.0 (HCO$_3^-$), for example within the ranges 12 to 14 (Na$^+$):9 to 11 (Cl$^-$):1 (K$^+$):3.2 to 3.6 (HCO$_3^-$).

The invention provides a solution in water comprising the following components at the following concentrations:
(a) N×(16 to 52) mmol/L PEG having an average molecular weight of 2500 to 4500;
(b1) N×(34 to 94) mmol/L sodium present as sodium ions;
(b2) N×(2.7 to 8.0) mmol/L potassium present as potassium ions;
(c) N×(30 to 76) mmol/L chloride ions;
(d) N×(7 to 26) mmol/L bicarbonate ions;
(e) N×an amount of preservative;
(f) optionally N×an amount of flavouring; and
(g) optionally N×an amount of sweetener
where N is in the range of 2 to 8.

The solution is a concentrate for N-fold dilution with water to provide a solution for ingestion comprising the following components at the following concentrations:
(a) 16 to 52 mmol/L PEG having an average molecular weight of 2500 to 4500;
(b1) 34 to 94 mmol/L sodium present as sodium ions;
(b2) 2.7 to 8.0 mmol/L potassium present as potassium ions;
(c) 30 to 76 mmol/L chloride ions;
(d) 7 to 26 mmol/L bicarbonate ions;
(e) an amount of preservative;
(f) optionally an amount of flavouring; and
(g) optionally an amount of sweetener.

The concentrate solution is preferably accompanied by instructions instructing the user to dilute with water by N-fold. N need not be an integer, but it is the same number for each component. Dilution of a solution of volume V by N-fold requires the addition of a volume (N−1)×V of water. Preferably N is from 3 to 7, for example from 4 to 6, for example 5.

Preferably, the concentration of PEG is N×(28 to 36) mmol/L, for example N×31.3 mmol/L. Preferably, the concentration of sodium ions is N×(49 to 80) mmol/L, more preferably N×(60 to 70) mmol/L, for example N×65 mmol/L. Preferably, the concentration of potassium ions is N×(3.8 to 6.0) mmol/L, more preferably N×(5.1 to 5.7) mmol/L, for example N×5.4 mmol/L. Preferably, the concentration of chloride ions is N×(40 to 66) mmol/L, more preferably N×(47 to 59) mmol/L, for example N×53 mmol/L. Preferably, the concentration of bicarbonate ions is N×(13 to 20) mmol/L, more preferably N×(15 to 19) mmol/L, for example N×17 mmol/L.

For example, the invention provides a solution in water comprising the following components at the following concentrations:
(a) 78 to 240 mmol/L PEG having an average molecular weight of 2500 to 4500;
(b1) 173 to 473 mmol/L sodium present as sodium ions;
(b2) 13 to 40 mmol/L potassium present as potassium ions;

(c) 150 to 382 mmol/L chloride ions;
(d) 36 to 131 mmol/L bicarbonate ions;
(e) preservative;
(f) optional flavouring; and
(g) optional sweetener.

Solutions of the invention preferably comprise sodium present as sodium ions in an amount of 173 to 473 mmol per liter, preferably within a range wherein the lower limit is 231, 259, 282 or 305 mmol per liter and the upper limit is, independently, 427, 398, 369 or 345 mmol per liter; for example 305 to 345 mmol per liter. For example, a solution of the invention may comprise approximately 325 mmol sodium present as sodium ions per liter.

In one embodiment, solutions of the invention preferably comprise potassium present as potassium ions in an amount of 14 to 43 mmol per liter, preferably within a range wherein the lower limit is 17, 23 or 26 mmol per liter and the upper limit is, independently, 39, 34 or 29 mmol per liter; for example from 26 to 29 mmol per liter. For example a solution of the invention may comprise approximately 27 mmol potassium present as potassium ions per liter.

In another embodiment, solutions of the invention preferably comprise potassium present as potassium ions in an amount of 13 to 40 mmol per liter, preferably within a range wherein the lower limit is 16, 19, 21, 23 or 24 mmol per liter and the upper limit is, independently, 36, 34, 31, 28 or 27 mmol per liter; for example 21 to 28 mmol per liter, for example from 24 to 25 mmol per liter. For example a solution of the invention may comprise approximately 25 mmol potassium present as potassium ions per liter.

Solutions of the invention preferably comprise chloride ions in an amount of 150 to 382 mmol per liter, preferably within a range wherein the lower limit is 187, 207, 226 or 245 mmol per liter and the upper limit is, independently, 344, 325, 305 or 284 mmol per liter; for example from 246 to 281 mmol per liter. For example a solution of the invention may comprise approximately 265 mmol chloride ions per liter.

Solutions of the invention preferably comprise bicarbonate ions in an amount of 36 to 131 mmol per liter, preferably within a range wherein the lower limit is 60, 71, 77 or 83 mmol per liter and the upper limit is, independently, 119, 107, 95 or 89 mmol per liter; for example 77 to 95 mmol per liter. For example a solution of the invention may comprise approximately 85 mmol per liter.

Solutions of the invention optionally comprise one or more flavourings. Flavourings assist in making the solutions in their diluted form for ingestion more palatable to certain patients.

The exact level of flavouring required depends on the intensity of flavour desired, and the nature and strength of the flavour in question. Typically, a flavouring may be present at a level of $N \times (0.2$ to $2)$ g per liter, for example 1 to 10 g per liter, for example from 1 to 5 g per liter, especially from 2 to 4 g per liter, for example 3.2 g per liter. Examples of flavours that can be used include orange, lemon-lime, lemon, citrus, chocolate, tropical fruit, aloe vera, tea, strawberry, grapefruit, blackcurrant, pineapple and vanilla. Preferred flavours are orange juice flavour and tropical fruit flavour. Citrus flavour may also be used.

Those and further suitable flavourings are available from various flavour manufacturers and suppliers, for example International Flavours and Fragrances Inc. (Duddery Hill, Haverhill, Suffolk, CB9 8LG, England), Ungerer & Company (Sealand Road, Chester, England CH1 4LP), Firmenich (Firmenich UK Ltd., Hayes Road, Southall, Middlesex UB2 5NN) or S. Black Ltd (Foxholes Business Park, John Tate Road, Hertford, Herts, SG13 7YH, United Kingdom).

Solutions of the invention may comprise one or more sweeteners. Preferred sweeteners include aspartame, acesulfame potassium (acesulfame K), sucralose and saccharine and combinations thereof. For example, solutions of the invention may comprise one or both of sucralose and acesulfame potassium (acesulfame K). Typically, a sweetener may be present at a level of $N \times (0.02$ to $0.2)$ g per liter, for example 0.1 to 1 g per liter In an embodiment, acesulfame K is present in an amount of $N \times (0.04$ to $0.12)$ g per liter, preferably 0.20 to 0.60 g per liter, preferably within in a range in which the lower limit is 0.20, 0.30 or 0.35 g per liter and the upper limit is, independently, 0.60, 0.50 or 0.45 g per liter. For example, a solution of the invention may comprise 0.40 g acesulfame K per liter.

In one embodiment, solutions of the invention preferably comprise acesulfame ions in an amount of 1.0 to 3.0 mmol per liter, preferably within in a range in which the lower limit is 1.0, 1.5 or 1.7 mmol per liter and the upper limit is, independently, 3.0, 2.5 or 2.2 mmol per liter. For example, a solution of the invention may comprise approximately 2.0 mmol acesulfame ions per liter.

In one embodiment, the invention provides a solution in water comprising the following components at the following concentrations:

(a) $N \times (16$ to $52)$ mmol/L PEG having an average molecular weight of 2500 to 4500;
(b1) $N \times (34$ to $94)$ mmol/L sodium present as sodium ions;
(c1) $N \times (2.7$ to $8.0)$ mmol/L potassium present as potassium ions;
(b2) $N \times (30$ to $76)$ mmol/L chloride ions;
(d) $N \times (7$ to $26)$ mmol/L bicarbonate ions;
(e) $N \times $ an amount of preservative;
(f) optionally $N \times $ an amount of flavouring; and
(g1) $N \times (0.29$ to $0.45)$ mmol/L acesulfame ions;
(g2) optionally $N \times $ an amount of additional sweetener
where N is in the range of 2 to 8.

The solution is a concentrate for N-fold dilution with water to provide a solution for ingestion comprising the following components at the following concentrations:

(a) 16 to 52 mmol/L PEG having an average molecular weight of 2500 to 4500;
(b1) 34 to 94 mmol/L sodium present as sodium ions;
(c1) 2.7 to 8.0 mmol/L potassium present as potassium ions;
(b2) 30 to 76 mmol/L chloride ions;
(d) 7 to 26 mmol/L bicarbonate ions;
(e) an amount of preservative;
(f) optionally an amount of flavouring; and
(g1) 0.29 to 0.45 mmol/L acesulfame ions;
(g2) optionally an amount of additional sweetener The concentrate solution is preferably accompanied by instructions instructing the user to dilute with water by N-fold. N need not be an integer, but it is the same number for each component. Dilution of a solution of volume V by N-fold requires the addition of a volume $(N-1) \times V$ of water. Preferably N is from 3 to 7, for example from 4 to 6, for example 5.

For example, in one embodiment the invention provides a solution in water, comprising the following components at the following concentrations:

(a) 78 to 240 mmol/L PEG having an average molecular weight of 2500 to 4500;
(b1) 173 to 473 mmol/L sodium present as sodium ions;
(c) 14 to 43 mmol/L potassium present as potassium ions;

(b2) 150 to 382 mmol/L chloride ions;
(d) 36 to 131 mmol/L bicarbonate ions;
(e) preservative;
(f) optional flavouring; and
(g1) 1.0 to 3.0 mmol/L acesulfame ions;
(g2) optional additional sweetener.

In one embodiment of a solution of the invention, the molar ratio of the individual ions in the components sodium chloride, potassium chloride, sodium bicarbonate and acesulfame K is preferably approximately 65 ($Na^+$):53 ($Cl^-$):5.4 ($K^+$):17 ($HCO_3^-$), ie approximately 12 ($Na^+$):10 ($Cl^-$):1 ($K^+$):3 ($HCO_3^-$), For example it may be within the ranges 10 to 14 ($Na^+$):8 to 12 ($Cl^-$):1 ($K^+$):2.5 to 3.7 ($HCO_3^-$), for example within the ranges 11 to 13 ($Na^+$):9 to 11 ($Cl^-$):1 ($K^+$):2.9 to 3.3 ($HCO_3^-$).

In an embodiment, sucralose is present in an amount of N×(0.012 to 0.04) g per liter, preferably 0.06 to 0.20 g per liter, preferably within in a range in which the lower limit is 0.06, 0.08 or 0.10 g per liter and the upper limit is, independently, 0.20, 0.18, 0.16 or 0.14 g per liter. For example, a solution of the invention may comprise 0.12 g sucralose per liter.

In an embodiment, the solution comprises both sucralose and acesulfame potassium (acesulfame K). Preferably, acesulfame K is present in an amount of 0.20 to 0.60 g per liter and sucralose is present in an amount of 0.06 to 0.20 g per liter. Preferably acesulfame K is present in an amount within a range in which the lower limit is 0.20, 0.30 or 0.35 g per liter and the upper limit is, independently, 0.60, 0.50 or 0.45 g per liter, and sucralose is present in an amount within a range in which the lower limit is 0.06, 0.08 or 0.10 g per liter and the upper limit is, independently, 0.20, 0.18, 0.16 or 0.14 g per liter. For example, a solution of the invention may comprise 0.40 g acesulfame K per liter and 0.12 g sucralose per liter.

Solutions of the invention are preferably substantially free from added citrate ions. Citrate ions are provided for example by citric acid and sodium citrate. Some fruit flavourings may intrinsically contain a small amount of citric acid. Those amounts are not considered substantial in this context. Solutions of the invention are preferably substantially free from added acid. Hydrogen ions are provided for example by organic acids (for example citric acid or ascorbic acid) or inorganic acids (for example hydrochloric acid). Some fruit flavourings may intrinsically contain small amounts of organic acids. Those amounts are not considered substantial in this context. Solutions of the invention preferably have a pH of 8.0 to 11.0, preferably 8.0 to 10.5, for example 8.4 to 9.0. Measurements of pH may, for example, be carried out with a Hanna Instruments "pH ep" temperature compensating pH meter.

The invention further provides a method of preparing a concentrate solution of the invention comprising combining the following components with water to the following concentrations:
(a) N×(70 to 130) g/L PEG having an average molecular weight of 2500 to 4500;
(b) N×(1.6 to 4.0) g/L sodium chloride;
(c) N×(0.2 to 0.6) g/L potassium chloride;
(d) N×(0.6 to 2.2) g/L sodium bicarbonate;
(e) N×an amount of preservative;
(f) optionally N×an amount of flavouring; and
(g) optionally N×an amount of sweetener
where N is in the range of 2 to 8.

For example, the method comprises combining the following components with water to the following concentrations:
(a) 350 to 600 g/L PEG having an average molecular weight of 2500 to 4500;
(b) 8.0 to 20 g/L sodium chloride;
(c) 1.0 to 3.0 g/L potassium chloride;
(d) 3.0 to 11 g/L sodium bicarbonate;
(e) preservative;
(f) optional flavouring; and
(g) optional sweetener.

Depending on the identities of the preservative, optional flavouring or optional sweetener and the amounts of the components, it may be beneficial to warm the liquid mixture during the method of preparing the concentrate. For example, it may be beneficial to warm the water (or a portion of it) to dissolve the preservative prior to combining the preservative with one or more other component of the concentrate. It is found that to prepare one liter of a concentrate solution comprising (a) 525 g/L PEG having an average molecular weight of 2500 to 4500; (b) 14.028 g/L sodium chloride; (c) 1.864 g/L potassium chloride; (d) 7.140 g/L sodium bicarbonate; (e) 2.5 or 3.5 g/L preservative; (f) 3.2 g/L flavouring; and (g) 0.52 g/L sweetener (for example it may comprise 0.40 g/L acesulfame K and 0.12 g/L sucralose), approximately 549 ml of water are needed.

In certain settings, where a concentrate solution is to be used soon after it has been prepared, a concentrate solution might not require an added preservative component. Accordingly, there is provided a solution in water comprising the following components at the following concentrations:
(a) N×(70 to 130) g/L PEG having an average molecular weight of 2500 to 4500;
(b) N×(1.6 to 4.0) g/L sodium chloride;
(c) N×(0.2 to 0.6) g/L potassium chloride;
(d) N×(0.6 to 2.2) g/L sodium bicarbonate;
(f) optionally N×an amount of flavouring; and
(g) optionally N×an amount of sweetener
where N is in the range of 2 to 8.

The solution is a concentrate for N-fold dilution with water to provide a solution for ingestion comprising the following components at the following concentrations:
(a) 70 to 130 g/L PEG having an average molecular weight of 2500 to 4500;
(b) 1.6 to 4.0 g/L sodium chloride;
(c) 0.2 to 0.6 g/L potassium chloride;
(d) 0.6 to 2.2 g/L sodium bicarbonate;
(f) optionally an amount of flavouring; and
(g) optionally an amount of sweetener The concentrate solution is preferably accompanied by instructions instructing the user to dilute with water by N-fold. N need not be an integer, but it is the same number for each component. Dilution of a solution of volume V by N-fold requires the addition of a volume (N−1)×V of water. Preferably N is from 3 to 7, for example from 4 to 6, for example 5.

For example, such a solution has the following components at the following concentrations:
(a) 350 to 600 g/L PEG having an average molecular weight of 2500 to 4500;
(b) 8.0 to 20 g/L sodium chloride;
(c) 1.0 to 3.0 g/L potassium chloride;
(d) 3.0 to 11 g/L sodium bicarbonate;
(f) optional flavouring; and
(g) optional sweetener.

In all respects other than in relation to the added preservative component, the solution has the preferred features described elsewhere herein. Containers and kits comprising such solutions, methods of preparing such solutions are also provided.

A preferred embodiment of a solution of the invention is a solution in water comprising the following components at the following concentrations:
(a) 525 g/L PEG having an average molecular weight of 2500 to 4500;
(b) 14.028 g/L sodium chloride;
(c) 1.864 g/L potassium chloride;
(d) 7.140 g/L sodium bicarbonate;
(e) preservative;
(f) optional flavouring; and
(g) optional sweetener.

For example, the preservative may be present in a concentration of 2.5 or 3.5 g/L. For example, the flavouring may be present in a concentration of 3.2 g/L. For example, the sweetener may be present in a concentration of 0.52 g/L (for example it may comprise 0.40 g acesulfame K and 0.12 g sucralose). Such a solution is typically diluted five-fold for use.

A preferred embodiment of a solution of the invention is a solution in water comprising the following components at the following concentrations:
(a) 420 g/L PEG having an average molecular weight of 2500 to 4500;
(b) 11.2224 g/L sodium chloride;
(c) 1.4912 g/L potassium chloride;
(d) 5.712 g/L sodium bicarbonate;
(e) preservative;
(f) optional flavouring; and
(g) optional sweetener.

For example, the preservative may be present in a concentration of 2.0 or 2.8 g/L. For example, the flavouring may be present in a concentration of 2.56 g/L. For example, the sweetener may be present in a concentration of 0.416 g/L (for example it may comprise 0.32 g acesulfame K and 0.096 g sucralose). Such a solution is typically diluted four-fold for use.

As discussed above, in use, the solution of the invention is combined with additional water to provide a medicament for drinking by a patient. A solution of the invention is, for example, diluted with approximately four times its volume of water to generate an approximately five-fold diluted solution (for the case when N=5). For example, a 25 ml unit of the solution may be diluted with from 75 to 125 ml of water to give a solution of from 100 ml to 150 ml. Particularly in the domestic setting, very accurate dilution is not generally possible or convenient. In patient instructions, the dilution step might be referred to as diluting a 25 ml unit of solution (which might be referred to as "5 teaspoons") with water to make a 125 ml solution (which might be referred to as "approximately half a glass of solution"). For example, a 25 ml unit of solution is diluted in 100 ml of water to give 125 ml of final solution for drinking.

A typical dose is 125 ml of diluted solution, and such a dose preferably contains the active ingredients in the amounts shown in the Table below (in addition to any preservative, flavouring and sweetener). As the absence of the Acesulfame K sweetener in a MOVICOL PLAIN solution makes it necessary to increase the amount of potassium chloride, a separate set of amounts is shown for a "plain" solution. In an alternative setting (for example for paediatric use or in patients with mild constipation), a typical dose is 62.5 ml of diluted solution and such a dose preferably contains the alternative amounts of active ingredients shown in the Table below:

| Component | Amount/g per 125 ml | | Amount/g per 62.5 ml | |
| --- | --- | --- | --- | --- |
| | With sweetener/flavouring | "plain" | With sweetener/flavouring | "plain" |
| PEG 3350 | 13.1250 | 13.1250 | 6.563 | 6.563 |
| Sodium Chloride | 0.3507 | 0.3508 | 0.1754 | 0.1754 |
| Potassium Chloride | 0.0466 | 0.0502 | 0.0233 | 0.0251 |
| Sodium Bicarbonate | 0.1785 | 0.1786 | 0.0893 | 0.0893 |

For the preparation of a 125 ml dose, an appropriate volume of the concentrate solution of the invention is diluted with water to make 125 ml.

Accordingly, the invention further provides a unit treatment of a solution of the invention, the unit treatment having the volume necessary to provide 11 to 15 g of PEG when diluted with water to 125 ml. An alternative unit treatment of a solution of the invention has the volume necessary to provide 5.5 to 7.5 g of PEG when diluted to 62.5 ml. For example, a unit treatment has the volume necessary to provide the components in the amounts shown in the table immediately above.

For example, a unit treatment may be from 10 to 50 ml of the concentrate solution of the invention. For example, if a solution of the invention comprises 525 g of PEG 3350 per liter, then 25 ml are required to provide the amount of PEG shown in the table above. A unit treatment is thus preferably from 20 to 40 ml, for example 25 to 30 ml, especially 25 ml. Accordingly, the invention further provides a unit treatment of from 10 to 50 ml of the solution of the invention. Preferably, a unit treatment is from 20 to 40 ml, for example 25 to 30 ml, especially 25 ml. For use in an alternative setting (for example for paediatric use or in patients with mild constipation) mentioned above, all of the quantities in a unit treatment are halved.

The invention provides a unit treatment comprising 7.8 to 62.5 ml of water comprising the following components at the following concentrations:
(a) N×(70 to 130) g/L PEG having an average molecular weight of 2500 to 4500;
(b) N×(1.6 to 4.0) g/L sodium chloride;
(c) N×(0.2 to 0.6) g/L potassium chloride;
(d) N×(0.6 to 2.2) g/L sodium bicarbonate;
(e) N×an amount of preservative;
(f) optionally N×an amount of flavouring; and
(g) optionally N×an amount of sweetener
where N is in the range of 2 to 8.

For example, a unit treatment may comprise 10 to 50 ml of a solution in water comprising the following components at the following concentrations:
(a) 350 to 600 g/L PEG having an average molecular weight of 2500 to 4500;
(b) 8.0 to 20 g/L sodium chloride;
(c) 1.0 to 3.0 g/L potassium chloride;
(d) 3.0 to 11 g/L sodium bicarbonate;
(e) preservative;
(f) optional flavouring; and
(g) optional sweetener.

In preferred aspects, the solution in a unit treatment has the features mentioned above in relation to the solutions of the invention.

A unit treatment may comprise 7.8 to 62.5 ml, for example 10 to 50 ml of a solution in water comprising the following components in the following weights:

(a) 3.50 to 30 g PEG having an average molecular weight of 2500 to 4500;
(b) 0.08 to 1.0 g sodium chloride;
(c) 0.01 to 0.15 g potassium chloride;
(d) 0.03 to 0.55 g sodium bicarbonate;
(e) preservative;
(f) optional flavouring; and
(g) optional sweetener.

A preferred unit treatment comprises 10 to 50 ml of a solution in water comprising the following components in the following weights:
(a) 11 to 15 g PEG having an average molecular weight of 2500 to 4500;
(b) 0.3 to 0.4 g sodium chloride;
(c) 0.035 to 0.055 g potassium chloride;
(d) 0.15 to 0.25 g sodium bicarbonate;
(e) preservative;
(f) optional flavouring; and
(g) optional sweetener.

A preferred unit treatment comprises 20 to 50 ml of a solution in water comprising the following components in the following weights:
(a) 13.125 g PEG having an average molecular weight of 3350;
(b) 0.3507 g sodium chloride;
(c) 0.0466 g potassium chloride;
(d) 0.1785 g sodium bicarbonate;
(e) preservative;
(f) optional flavouring; and
(g) optional sweetener.

Such a unit treatment is, for example, for dilution with water in a volume dependent on the concentration of the ingredients. A 20 ml unit treatment would typically be combined with 105 ml of water; a 25 ml unit treatment would typically be combined with 100 ml of water; a 30 ml unit treatment would typically be combined with 95 ml of water; a 40 ml unit treatment would typically be combined with 85 ml of water and a 50 ml unit treatment would typically be combined with 75 ml of water.

For use in an alternative setting (for example for paediatric use or in patients with mild constipation) mentioned above, all of the quantities in a unit treatment are halved. Thus, an alternative preferred unit treatment comprises 10 to 25 ml of a solution in water comprising the following components in the following weights:
(a) 6.563 g PEG having an average molecular weight of 3350;
(b) 0.01754 g sodium chloride;
(c) 0.0233 g potassium chloride;
(d) 0.0893 g sodium bicarbonate;
(e) preservative;
(f) optional flavouring; and
(g) optional sweetener.

Such a unit treatment is, for example, for dilution with water in a volume dependent on the concentration of the ingredients. A 10 ml unit treatment would typically be combined with 52.5 ml of water; a 15 ml unit treatment would typically be combined with 47.5 ml of water; a 20 ml unit treatment would typically be combined with 42.5 ml of water; a 25 ml unit treatment would typically be combined with 37.5 ml of water.

As mentioned above, the invention provides a container containing a solution of the invention. Such a container may, for example, contain:
(a) N×(10 to 16) g PEG having an average molecular weight of 2500 to 4500;
(b) N×(0.26 to 0.44) g sodium chloride;
(c) N×(0.035 to 0.056) g potassium chloride;
(d) N×(0.14 to 0.22) g sodium bicarbonate;
(e) N×an amount of preservative;
(f) optionally N×an amount of flavouring; and
(g) optionally N×an amount of sweetener
(h) water to a volume V
wherein is N is 1 to 80, V is 20 ml to 1000 ml, and V(in ml) is such that V/N≤67.5.

For example, a container may contain:
(a) x×262.50 g polyethylene glycol (PEG) 3350;
(b) x×7.014 g sodium chloride;
(c) x×0.932 g potassium chloride;
(d) x×3.570 g sodium bicarbonate;
(e) x×an amount of preservative;
(f) optionally x×an amount of flavouring;
(g) optionally x×an amount of sweetener; and
(h) water to x×500 ml;
Where x is 0.5 to 2, for example x is 0.5 or 1.

Such a container may, for example, contain:
(a) 262.50 g PEG 3350;
(b) 7.014 g sodium chloride;
(c) 0.932 g potassium chloride;
(d) 3.570 g sodium bicarbonate;
(e) preservative;
(f) optional flavouring;
(g) optional sweetener; and
(h) water to 500 ml An alternative container may contain:
(a) 131.25 g PEG 3350;
(b) 3.507 g sodium chloride;
(c) 0.466 g potassium chloride;
(d) 1.785 g sodium bicarbonate;
(e) preservative;
(f) optional flavouring;
(g) optional sweetener; and
(h) water to 250 ml An alternative container may contain:
(a) 78.75 g PEG 3350;
(b) 2.1042 g sodium chloride;
(c) 0.2796 g potassium chloride;
(d) 1.071 g sodium bicarbonate;
(e) preservative;
(f) optional flavouring;
(g) optional sweetener; and
(h) water to 150 ml An alternative container may contain:
(a) 52.5 g PEG 3350;
(b) 1.4028 g sodium chloride;
(c) 0.1864 g potassium chloride;
(d) 0.714 g sodium bicarbonate;
(e) preservative;
(f) optional flavouring;
(g) optional sweetener; and
(h) water to 100 ml In such containers, preferred amounts and identities of preservative, flavouring and sweetener are as described above in relation to solutions of the invention, adjusted where necessary for the amount of water in the containers.

The solutions of the present invention, optionally presented in a container comprising multiple treatment units, are preferably provided with instructions for use. The instructions may instruct the user to dilute a stated volume of the solution of the invention with a stated volume of water. For example, the instructions may instruct the user to dilute the solution to a volume of 125 ml for use. If the solution of the invention comprises 525 g of PEG 3350 per liter, then 25 ml are required to provide the amount of PEG shown in the table above, and the instructions may instruct the user to dilute 25 ml of the solution with 100 ml of water. 25 ml equates to 5 conventional teaspoons. 100 ml equates to a conventional "half glassful of water". For the level of accuracy typically required for this form of medication, approximate units of volume such as "teaspoons" and "glasses" are generally adequate, and patient information may be appropriately phrased. For use in an alternative setting (for example for paediatric use or in patients with mild constipation) mentioned above, the instructions may instruct the user to dilute 12.5 ml of the solution with 50 ml of water. 12.5 ml equates to 2.5 conventional teaspoons. 50 ml equates to a conventional "quarter glassful of water".

The invention further provides a kit comprising a container containing a solution of the invention together with instructions as set out above, for example instructing the user to dilute a stated volume of the solution of the invention with a particular volume of water. The invention further provides a kit comprising a container containing a solution of the invention together with a measuring accessory for measuring out a defined volume of the solution. Examples of measuring accessories include measuring cups, measuring spoons, measuring tubes, and syringes. If the solution of the invention comprises 525 g of PEG 3350 per liter, then 25 ml are required to provide the amount of PEG shown in the table above. Thus, the measuring accessory preferably enables the measurement of a 25 ml unit treatment out of the bottle.

The measuring accessory may be adapted to attach to the container, for example it may be in the form of a cap that fits over and grips onto the closure of the container in storage and can be held separately from the container for measuring out a required volume of solution. The measuring accessory may have a measurement volume such that several measurement accessories-ful provide the required unit treatment volume. For example, for the provision of a 25 ml unit treatment volume, a measuring accessory might provide for measuring a volume of 25 ml, 12.5 ml (two needed), 8.333 ml (three needed), 6.25 ml (4 needed) or 5 ml (5 needed). A suitable measuring accessory may have the required volume as its total capacity, or it may be provided with one or more gradation lines to indicate the required volume. In one embodiment, the measuring accessory is a cap that provides for the measurement of a 25 ml unit volume. For use in an alternative setting (for example for paediatric use or in patients with mild constipation) mentioned above, the volumes mentioned here are all halved. For distribution and sale, a container may be provided in an outer packaging, such as a carton. Instructions may be provided on a medium, for example paper, inside the outer packaging. Instructions may be printed onto the outer packaging, or onto the container itself. A carton may contain the container, a measuring accessory and instructions.

The invention provides a method of preparing a solution for the treatment of constipation or faecal impaction, which method comprises combining a volume (for example a treatment unit volume) of a solution of the invention with water. The invention provides a method of preparing a laxative solution comprising combining a volume (for example a treatment unit volume) of a solution of the invention with water. The invention further provides a laxative solution or a faecal impaction treatment solution that has been prepared by combining a solution of the invention with water.

After a solution of the invention has been diluted by combining with water, the resultant laxative solution is suitable for use in the treatment of constipation or faecal impaction. Accordingly, the present invention also provides a method of treating constipation or faecal impaction comprising administering orally to a subject a laxative solution prepared by combining a solution of the invention with water. The invention also provides a solution prepared by combining a solution of the invention with water for use as a medicament; for example the medicament can be for use in the treatment of constipation or faecal impaction. A solution for use in a method of the invention has the preferred features described above in respect of the solutions of the invention.

In a preferred regime a patient is instructed to take 25 ml of a solution of the invention diluted in 100 ml water 1-3 times daily in divided doses, according to the individual response or the severity of the constipation. For the treatment of faecal impaction, a patient is instructed to take 25 ml of a solution of the invention diluted in 100 ml water 1-8 times daily, according to the individual response or the severity of the faecal impaction.

The invention further provides a solution in water, of the following components at the following concentrations:
(a) 70 to 130 g/L PEG having an average molecular weight of 2500 to 4500;
(b) 1.6 to 4.0 g/L sodium chloride;
(c) 0.2 to 0.6 g/L potassium chloride;
(d) 0.6 to 2.2 g/L sodium bicarbonate;
(e) optional preservative;
(f) optional flavouring; and
(g1) sucralose
(g2) optional additional sweetener.

The solution has been found to have a particularly acceptable taste. Sucralose may, for example, be present in an amount of 0.012 to 0.04 g per liter, preferably within in a range in which the lower limit is 0.012, 0.016 or 0.020 g per liter and the upper limit is, independently, 0.004, 0.036, 0.032 or 0.028 g per liter. For example, such a solution may comprise 0.024 g sucralose per liter. The solution may comprise optional preservative (e), optional flavouring (f) and optional additional sweetener (g2) of the types described elsewhere herein. The concentrations of the components (a) to (g2) in such a solution are preferably the amounts arrived at after dilution of a concentrate solution of the invention described above, for example the concentration of a component may be one fifth of the concentration described above for that component in relation to a concentrate solution of the invention. The solution is suitable for use as a medicament, for example for the treatment of constipation, or faecal impaction, and a method of treatment of such conditions is also provided. The stated components may be provided in a form for combination with water to provide such a solution. For example, the components may be provided as a concentrated solution in water, or as a dry powder. A dry powder may be provided in a sachet, for example containing a unit dose. For example a sachet may contain 13.1250 g Macrogol (Polyethylene glycol) 3350, 0.3507 g sodium chloride, 0.1785 g sodium bicarbonate, 0.0466 or 0.0502 g potassium chloride and sucralose.

The invention further provides a solution in water, of the following components at the following concentrations:
(a) 70 to 130 g/L PEG having an average molecular weight of 2500 to 4500;
(b) 1.6 to 4.0 g/L sodium chloride;
(c) 0.2 to 0.6 g/L potassium chloride;
(d) 0.6 to 2.2 g/L sodium bicarbonate;
(e) optional preservative;
(f) flavouring selected from orange juice and tropical fruit; and
(g) optional sweetener.

The solution has been found to have a particularly acceptable taste. The flavouring selected from orange juice and tropical fruit flavouring may be present at a level of from 0.2 to 2.0 g per liter, for example from 0.2 to 1 g per liter, especially from 0.4 to 0.8 g per liter, for example 0.64 g per liter. The solution may comprise optional preservative (e) and optional sweetener (g) of the types described elsewhere herein. The concentrations of the components (a) to (g) in such a solution are preferably the amounts arrived at after dilution of a concentrate solution of the invention described above, for example the concentration of a component may be one fifth of the concentration described above for that component in relation to a concentrate solution of the invention. The solution is suitable for use as a medicament, for example for the treatment of constipation, or faecal impaction, and a method of treatment of such conditions is also provided. The stated components may be provided in a form for combination with water to provide such a solution. For example, the components may be provided as a concentrated solution in water, or as a dry powder. A dry powder may be provided in a sachet, for example containing a unit dose. For example a sachet may contain 13.1250 g Macrogol (Polyethylene glycol) 3350, 0.3507 g sodium chloride, 0.1785 g sodium bicarbonate, 0.0466 or 0.0502 g potassium chloride and flavouring selected from orange juice and tropical fruit.

EXAMPLES

The following non-limiting Examples illustrate the invention. All of the solutions in the Examples comprise the components of Table 1.

TABLE 1

Common components of the solutions of the Examples

| Component | Quantity/g |
|---|---|
| PEG 3350 | 13.1250 |
| Sodium Chloride | 0.3507 |
| Potassium Chloride | 0.0466* |
| Sodium Bicarbonate | 0.1785 |
| Acesulfame K | 0.0100** |
| Optional Preservative | As indicated |
| Optional Flavour | As indicated |
| Optional Additional Sweenter | As indicated |
| Water | As indicated |

*different amount was used in Solution 1B;
**absent from Solution 1B

Examples 1, 2 and 3

Microbiological Testing of Solutions

In each of Examples 1, 2 and 3 that follow, the microbiological testing was carried out as follows:
The microbiological condition of the samples was determined following the European Pharmacopoeia (EP) 5.6 Section 2.6 12 "Microbiological Examination of Non-Sterile Products (Total Viable Aerobic Count)". In each case in Examples 1, 2 and 3, no microbial contaminants could be detected in the samples and they were concluded to be in good visible and microbiological condition containing less than 10 colony forming units per g (CFU/g). In some, but not all instances, the pH of the sample was measured. pH measurements can be carried out with a Hanna Instruments "pH ep" temperature compensating pH meter. In some instances, the pH of a sample was adjusted before the testing was commenced (as indicated).

Microbial Challenge Test Protocol:
Five 20 g portions of each sample were transferred to sterile glass bottles and inoculated separately with 0.2 ml culture of the test species as detailed below. The test species used include the following shown in Table 2, which are referred to in the Table with the abbreviations used hereinafter.

TABLE 2

| Species | Abbreviation |
|---|---|
| Pseudomonas aeruginosa | P |
| Escherichia coli | E |
| Staphylococcus aureus | S |
| Candida albicans | C |
| Aspergilus niger | A |

The inoculated sample portions were mixed using sterile implements and stored at room temperature. The challenge test protocol of the EP 1999 was then followed. In the results tables below, the initial innoculum level (in CFU/g) is given in the first column, and the numbers of CFU/g present after 14 and 28 days are given on the subsequent columns. For Candida albicans and Aspergilus niger, a "Factor" is given in the Tables. That factor is the multiple by which the numbers of CFU/g had been reduced from the initial innoculum level by 14 days. The EP Pass Criteria are as shown in Table 3 as set out in table 5.1.3-.3 Oral preparations in the European Pharmacopoeia (EP) 6.0, Section 5.1.3 "Efficacy of antimicrobial preservation".

TABLE 3

| | Log Drop from Baseline Value | |
|---|---|---|
| Test Species | 14 days | 28 days |
| Bacteria | 3 | NI |
| Yeasts/moulds | 1 | NI |

NI = no increase

Comparative Example 1

Microbiological Testing of Solutions Lacking Preservative

Solutions 1A and 1B were prepared, containing the components in the amounts shown in Table 1 above (except that, for solution 1B, there was no Acesulfame K, and the quantity of potassium chloride was 0.0502 g) together with the components in Table 4 per 32.5 ml. (1liter of solution was prepared in each case, containing a total weight of 424.95 g of solid in the case of 1A and 421.68 g of solid in the case of 1B).

TABLE 4

| Additional Component | Solution 1A (g/32.5 mL) | Solution 1B (g/32.5 mL) |
|---|---|---|
| Lemon-Lime Flavour | 0.1000 | — |
| Water | to 32.5 ml | to 32.5 ml |
| Measured pH | 8.8 | 8.8 |

The Lemon-Lime Flavour is the flavouring in the MOVICOL powder marketed in the UK by Norgine Limited (Chaplin House, Widewater Place, Moorhall Road, Harefield, Uxbridge, Middlesex UB9 6NS, United Kingdom). Solutions 1A and 1B are most readily prepared by dissolution of the commercially available MOVICOL Lemon-Lime flavour powder, and MOVICOL PLAIN (ie unflavoured) powder, respectively. Such solutions may be prepared by dissolving 20 commercially available sachets in water to 650 ml.

Test Results Table 5:

| Test Species and Initial Inoculum Level (CFU/g) | Solution 1A CFU per g after: | | Solution 1B CFU per g after: | |
|---|---|---|---|---|
| | 14 days | 28 days | 14 days | 28 days |
| P: NCTC 12924 $3.3 \times 10^7$ | <10 | <10 | <10 | <10 |
| E: NCTC 12923 $1.1 \times 10^6$ | <10 | <10 | <10 | <10 |
| S: NCTC 10788 $1.6 \times 10^6$ | <10 | <10 | <10 | <10 |
| C: NCPF 3179 $1.0 \times 10^6$ | $6.1 \times 10^4$ | $7.3 \times 10^3$ | $3.8 \times 10^5$ | $2.9 \times 10^5$ |
| A: NCPF 2275 $1.4 \times 10^5$ | $4.0 \times 10^4$ | $9.0 \times 10^3$ | $8.0 \times 10^4$ | $1.3 \times 10^4$ |
| C. Albicans Factor 14 d | 16 | | 2.6 | |
| A. Niger Factor 14 d | 3.5 | | 1.75 | |

The 1B solution did not achieve the required log reduction for yeast. The 1A solution did not achieve the required log reduction for either yeast or mould. Accordingly, the solutions without any preservative were found not to be suitable for use as concentrates for the preparation of oral medicaments.

Example 2

Microbiological Testing of Solutions Including Preservative

Solutions 2A to 2Q were prepared. Each solution contained the components shown in Table 1, together with the individual components shown in Tables 6a and 6b.

Sodium propyl paraben (sodium propyl 4-hydroxbenzoate) is available under the tradename Iscaguard PS. A blend of methyl paraben (18%), ethyl paraben (9%) and benzyl alcohol (73%) is available under the tradename Iscaguard MEB. Phenoxyethanol is available under the tradename Iscaguard PE. Methyl paraben is available under the tradename Iscaguard M. Ethyl paraben is available under the tradename Iscaguard E. Propyl paraben is available under the tradename Iscaguard P. A blend of methyl paraben (18%), ethyl paraben (9%) and phenoxyethanol (73%) is available under the tradename Iscaguard MEP. All of those Iscaguard products are available from ISCA UK Ltd (Nine Mile Point Industrial Estate, Crosskeys, Newport, NP11 7HZ, UK). A blend of methyl paraben (15%), ethyl paraben (10%) and phenoxyethanol (75%) is available from S. Black Ltd (Foxholes Business Park, John Tate Road, Hertford, Herts, SG13 7YH, United Kingdom) under the tradename Paratexin BSB.

In Tables 6a and 6b, the flavour "TF" is Tropical Fruit and the flavour "OJ" is Orange Juice. They are available from Firmenich UK Ltd. (Hayes Road, Southall, Middlesex UB2 5NN). A summary of the preservative efficacy test results (C. Albicans and A. Niger only) is shown in Tables 6a and 6b. Details are shown in tables 7 to 11b.

TABLE 6a

| Component | 2A | 2B | 2C | 2D | 2E | 2F | 2G | 2H |
|---|---|---|---|---|---|---|---|---|
| Flavour | None | None | 0.0375 gTF | 0.0375 gTF | 0.0375 gTF | 0.0375 gTF | 0.0375 gTF | 0.0375 gTF |
| Sucralose | None | None | 0.0150 g | 0.0150 g | 0.0150 g | 0.0150 g | 0.0150 g | 0.0150 g |
| Sodium propyl paraben (sodium propyl 4-hydroxybenzoate) | 0.05% [0.01625 g] | 0.1% [0.0325 g] | | | | | | |
| Blend of methyl paraben (18%), ethyl paraben (9%) and benzyl alcohol (73%) | | | 0.3% [0.075 g] | 0.5% [0.125 g] | 0.7% [0.175 g] | | | |
| Phenoxyethanol | | | | | | 0.7% [0.175 g] | | |
| Methyl paraben (as sodium salt) | | | | | | | 0.15% [0.0375 g] | |
| Ethyl paraben (as sodium salt) | | | | | | | 0.10% [0.025 g] | |
| Blend of methyl paraben (18%), ethyl paraben (9%) and phenoxyethanol (73%) | | | | | | | | 0.5% [0.125 g] |
| Water | to 32.5 ml | to 32.5 ml | to 25 ml | to 25 ml | to 25 ml | to 25 ml | to 25 ml | to 25 ml |
| pH | 8.8* | 8.8* | 8.8 | 8.8 | 8.7 | 7.0** | 7.0** | 8.7 |
| C. Albicans Factor 14 d | 10 | 39 | 1800 | 1500 | 2200 | 33000 | 26000 | >$10^5$ |
| A. Niger Factor 14 d | 1.4 | 2.0 | 330 | 100 | 440 | 2.0 | 9.2 | 91 |
| EP Protocol Pass | — | — | Pass | Pass | Pass | — | — | Pass |
| Table No | 7 | 7 | 8 | 8 | 8 | 9 | 9 | 10 |

*= adjusted to 8.8 with HCl.
**= adjusted to 7.0 with citric acid

Solutions 2A and 2B were prepared in 1l batches, solutions 2C, 2D, 2E and 2H were prepared in batches of 500 ml, and solutions 2F and 2G were prepared in batches of 200 ml.

TABLE 6b

| Component | 2I | 2J | 2K | 2L | 2M | 2N | 2P | 2Q |
|---|---|---|---|---|---|---|---|---|
| Flavour | 0.0375 gTF | 0.0375 gTF | 0.0800 gOJ | 0.0800 gOJ | 0.0800 gOJ | 0.0800 gOJ | 0.0800 gOJ | 0.0800 gOJ |
| Sucralose | 0.0150 g | 0.0150 g | 0.003 g | 0.003 g | 0.003 g | 0.003 g | 0.003 g | 0.003 g |

TABLE 6b-continued

| Component | 2I | 2J | 2K | 2L | 2M | 2N | 2P | 2Q |
|---|---|---|---|---|---|---|---|---|
| Methyl paraben | | | 0.18% [0.045 g] | 0.225% [0.05625 g] | 0.0675% [0.0169 g] | | 0.0675% [0.0169 g] | |
| Propyl paraben | | | 0.02% [0.005 g] | 0.025% [0.00625 g] | | | | |
| Ethyl paraben | | | | | | 0.0338% [0.0084 g] | | 0.0338% [0.0084 g] |
| Benzyl alcohol | | | | | | | 0.1825% [0.0456 g] | 0.2163% [0.05406 g] |
| Propylene glycol | | | 3.75 g | 3.75 g | | | | |
| Blend of methyl paraben (15%), ethyl paraben (10%) and phenoxyethanol (75%) | 0.5% [0.125 g] | 0.8% [0.200 g] | | | | | | |
| Water | to 25 ml 8.3 | to 25 ml 8.5 | to 25 ml | to 25 ml | to 25 ml | to 25 ml | to 25 ml | to 25 ml |
| C. Albicans Factor 14 d | >$10^5$ | >$10^5$ | >$10^5$ | >$10^5$ | >$10^5$ | >$10^5$ | >$10^5$ | >$10^5$ |
| A. Niger Factor 14 d | 14 | 25 | >$10^5$ | >$10^5$ Regrowth at 28 days | 3.0 | 3.8 | 2.6 | 5.3 |
| EP Protocol Pass | — | Pass | Pass | — | — | — | — | — |
| Table No | 10 | 10 | 11a | 11a | 11a | 11b | 11b | 11b |

Solutions 2I and 2J were prepared in batches of 500 ml. Solutions 2K, 2L, 2M, 2N, 2P and 2Q were prepared in batches of 250 ml.

Test Run II—Test Results Table 7:

| Test Species and Initial Inoculum Level (CFU/g) | Solution 2A CFU per g after: | | Solution 2B CFU per g after: | |
|---|---|---|---|---|
| | 14 days | 28 days | 14 days | 28 days |
| P: NCTC 12924 4.7 × $10^6$ | <10 | <10 | <10 | <10 |
| E: NCTC 12923 2.7 × $10^6$ | <10 | <10 | <10 | <10 |
| S: NCTC 10788 3.3 × $10^6$ | <10 | <10 | <10 | <10 |
| C: NCPF 3179 1.4 × $10^6$ | 1.4 × $10^5$ | 1.3 × $10^5$ | 3.6 × $10^4$ | 3.5 × $10^4$ |
| A: NCPF 2275 4.0 × $10^5$ | 2.8 × $10^5$ | 3.0 × $10^5$ | 2.0 × $10^5$ | 2.0 × $10^5$ |

Test Run III—Test Results Table 8:

| Test Species and Initial Inoculum Level (CFU/g) | Solution 2C CFU per g after: | | Solution 2D CFU per g after: | | Solution 2E CFU per g after: | |
|---|---|---|---|---|---|---|
| | 14 days | 28 days | 14 days | 28 days | 14 days | 28 days |
| P: NCTC 12924 3.8 × $10^6$ | <10 | <10 | <10 | <10 | <10 | <10 |
| E: NCTC 12923 6.0 × $10^6$ | <10 | <10 | <10 | <10 | <10 | <10 |
| S: NCTC 10788 4.2 × $10^6$ | 50 | <10 | 1.1 × $10^2$ | <10 | <10 | <10 |
| C: NCPF 3179 3.5 × $10^5$ | 1.9 × $10^2$ | <10 | 2.4 × $10^2$ | <10 | 1.6 × $10^2$ | <10 |
| A: NCPF 2275 4.0 × $10^5$ | 1.2 × $10^3$ | 10 | 4.0 × $10^3$ | 30 | 9.0 × $10^2$ | <10 |

Test Run IV—Test Results Table 9:

| Test Species and Initial Inoculum Level (CFU/g) | Solution 2F CFU per g after: | | Solution 2G CFU per g after: | |
|---|---|---|---|---|
| | 14 days | 28 days | 14 days | 28 days |
| P: ATCC 9027 1.9 × $10^6$ | <10 | <10 | <10 | <10 |
| S: ATCC 6538 1.5 × $10^6$ | 2.5 × $10^3$ | <10 | 6.8 × $10^5$ | 5.0 × $10^2$ |
| C: NCTC NCPF 3179 1.3 × $10^6$ | 40 | <10 | 50 | <10 |
| A: ATCC 16404 3.5 × $10^5$ | 1.8 × $10^5$ | 4.1 × $10^4$ | 3.8 × $10^4$ | 3.2 × $10^2$ |

Test Run V—Test Results Table 10:

| Test Species and Initial Inoculum Level (CFU/g) | Solution 2H CFU per g after: | | Solution 2I CFU per g after: | | Solution 2J CFU per g after: | |
|---|---|---|---|---|---|---|
| | 14 days | 28 days | 14 days | 28 days | 14 days | 28 days |
| P: NCTC 12924 $7.3 \times 10^7$ | <10 | <10 | <10 | <10 | <10 | <10 |
| E: NCTC 12923 $4.3 \times 10^6$ | <10 | <10 | <10 | <10 | <10 | <10 |
| S: NCTC 10788 $4.3 \times 10^6$ | <10 | <10 | $1.3 \times 10^4$ | <10 | $3.9 \times 10^2$ | <10 |
| C: NCPF 3179 $6.6 \times 10^6$ | <10 | <10 | 20 | <10 | <10 | <10 |
| A: NCPF 2275 $1.0 \times 10^5$ | $1.1 \times 10^3$ | <10 | $7.0 \times 10^3$ | $4.1 \times 10^3$ | $4.0 \times 10^3$ | $2.2 \times 10^2$ |

Test Run VI—Test Results Tables 11a and 11b:

| Test Species and Initial Inoculum Level (CFU/g) | Solution 2K CFU per g after: | | Solution 2L CFU per g after: | | Solution 2M CFU per g after: | |
|---|---|---|---|---|---|---|
| | 14 days | 28 days | 14 days | 28 days | 14 days | 28 days |
| P: NCTC 12924 $3.2 \times 10^6$ | <10 | <10 | <10 | <10 | <10 | <10 |
| E: NCTC 12923 $4.0 \times 10^6$ | <10 | <10 | <10 | <10 | <10 | <10 |
| S: NCTC 10788 $1.4 \times 10^6$ | <10 | <10 | <10 | <10 | <10 | <10 |
| C: NCPF 3179 $3.2 \times 10^6$ | <10 | <10 | <10 | <10 | <10 | <10 |
| A: NCPF 2275 $1.0 \times 10^6$ | <10 | <10 | <10 | 40 | $3.3 \times 10^5$ | $2.1 \times 10^4$ |

| Test Species and Initial Inoculum Level (CFU/g) | Solution 2N CFU per g after: | | Solution 2P CFU per g after: | | Solution 2Q CFU per g after: | |
|---|---|---|---|---|---|---|
| | 14 days | 28 days | 14 days | 28 days | 14 days | 28 days |
| P: NCTC 12924 $3.2 \times 10^6$ | <10 | <10 | <10 | <10 | <10 | <10 |
| E: NCTC 12923 $4.0 \times 10^6$ | <10 | <10 | <10 | <10 | <10 | <10 |
| S: NCTC 10788 $1.4 \times 10^6$ | <10 | <10 | <10 | <10 | <10 | <10 |
| C: NCPF 3179 $3.2 \times 10^6$ | <10 | <10 | 20 | <10 | <10 | <10 |
| A: NCPF 2275 $1.0 \times 10^6$ | $2.6 \times 10^5$ | $2.2 \times 10^4$ | $3.8 \times 10^5$ | $4.0 \times 10^4$ | $1.9 \times 10^5$ | 20 |

It is seen from the results in tables 7 to 11 (summarized in Table 6), that the majority of the preservatives achieved a reduction in the number of viable micro-organisms in the assays. It is seen that the combination of Blend of methyl paraben, ethyl paraben and benzyl alcohol was especially effective against the mould (*A. niger*).

The 2A, 2B, 2M, 2N, 2P and 2Q solutions did not achieve the required log reduction for mould (*A. niger*) to pass the European Pharmacopoeial criteria, though a reduction in the number of viable micro-organisms was observed. The 2F solution did not achieve the required log reduction for bacteria (*S. aureus*) or mould (*A. niger*) at the 14 day time point. Likewise, the 2G solution did not achieve the required log reduction for bacteria (*S. aureus*) or mould (*A. niger*) at the 14 day time point. Solution 2I also failed to achieve the required log reduction for the bacterium *S. aureus*. In solution 2L, re-growth of *A. niger* was observed.

Accordingly, although solutions 2A, 2B, 2F, 2G, 2I, 2L, 2M, 2N, 2P and 2Q showed a reduction in the number of viable micro-organisms for each organism, they were found not to be sufficiently preserved for oral pharmaceutical use with the tested level of preservative.

The 2C, 2D, 2E, 2H, 2J, and 2K solutions achieved the required log reduction for bacteria, yeast and mould. Accordingly, the solutions were found to be suitable for oral pharmaceutical use.

Example 3

Microbiological Testing of Solutions Including Methyl Paraben, Ethyl Paraben and Benzyl Alcohol Preservative Blend Solutions 3A to 3D were prepared. Each solution contained the components shown in Table 1, together with the individual components shown in Table 12.

TABLE 12

| Component | 3A | 3B | 3C | 3D |
|---|---|---|---|---|
| Flavour | 0.0800 g OJ | 0.0800 g OJ | 0.0800 g OJ | 0.0800 g OJ |
| Sucralose | 0.0030 g | 0.0030 g | 0.0030 g | 0.0030 g |
| Blend of methyl paraben (18%), ethyl paraben (9%) and benzyl alcohol (73%) | 0.1% [0.025 g] | 0.15% [0.0375 g] | 0.2% [0.050 g] | 0.25% [0.0625 g] |
| Water | to 25 ml | to 25 ml | to 25 ml | to 25 ml |
| C. Albicans Factor 14 d | 2000 | 4100 | 2200 | 2700 |
| A. Niger Factor 14 d | 8.5 | 5.7 | 8.5 | 11 |
| EP Protocol Pass | — | — | — | Pass |
| Table No | 13a | 13a | 13b | 13b |

In Table 12, the flavour "OJ" is Orange Juice flavour, available from Firmenich UK Ltd. (Hayes Road, Southall, Middlesex UB2 5NN).

Solutions 3A to 3D were each prepared as 200 ml batches.

Test Run VII—Test Results Tables 13a and 13b:

| Test Species and Initial Inoculum Level (CFU/g) | Solution 3A CFU per g after: | | Solution 3B CFU per g after: | |
|---|---|---|---|---|
| | 14 days | 28 days | 14 days | 28 days |
| P: NCTC 12924 $7.9 \times 10^6$ | <10 | <10 | <10 | <10 |
| E: NCTC 12923 $9.2 \times 10^6$ | <10 | <10 | <10 | <10 |
| S: NCTC 10788 $1.1 \times 10^7$ | $1.4 \times 10^3$ | <10 | $1.6 \times 10^3$ | <10 |
| C: NCPF 3179 $1.9 \times 10^6$ | $9.7 \times 10^2$ | <10 | $4.6 \times 10^2$ | <10 |
| A: NCPF 2275 $3.4 \times 10^5$ | $4.0 \times 10^4$ | $1.0 \times 10^4$ | $6.0 \times 10^4$ | $4.0 \times 10^4$ |

| Test Species and Initial Inoculum Level (CFU/g) | Solution 3C CFU per g after: | | Solution 3D CFU per g after: | |
|---|---|---|---|---|
| | 14 days | 28 days | 14 days | 28 days |
| P: NCTC 12924 $7.9 \times 10^6$ | <10 | <10 | <10 | <10 |
| E: NCTC 12923 $9.2 \times 10^6$ | <10 | <10 | <10 | <10 |
| S: NCTC 10788 $1.1 \times 10^7$ | $7.0 \times 10^2$ | <10 | $1.4 \times 10^3$ | 10 |
| C: NCPF 3179 $1.9 \times 10^6$ | $8.5 \times 10^2$ | <10 | $7.0 \times 10^2$ | <10 |
| A: NCPF 2275 $3.4 \times 10^5$ | $4.0 \times 10^4$ | $1.1 \times 10^4$ | $3.0 \times 10^4$ | $4.0 \times 10^3$ |

Solutions 3E to 3G were prepared. Each solution contained the components shown in Table 1, together with the individual components shown in Table 14.

TABLE 14

| Component | 3E (comparative Example) | 3F | 3G |
|---|---|---|---|
| Flavour | 0.0800 g TF | 0.0800 g TF | 0.0800 g TF |
| Sucralose | 0.0030 g | 0.0030 g | 0.0030 g |
| Blend of methyl paraben (18%), ethyl paraben (9%) and benzyl alcohol (73%) | None | 0.30% [0.075 g] | 0.35% [0.0875 g] |
| Water | to 25 ml | to 25 ml | to 25 ml |
| C. Albicans Factor 14 d | 2500 | 1900 | 700 |
| A. Niger Factor 14 d | 7 | 25 | 29 |
| EP Protocol Pass | — | Pass | Pass |
| Table No | 15 | 15 | 15 |

In Table 14, the flavour "TF" is Tropical Fruit, available from Firmenich UK Ltd. (Hayes Road, Southall, Middlesex UB2 5NN).

Solutions 3E to 3G were each prepared as 500 ml batches by adding preservative to 500 ml of a stock solution of the other components, the stock solution having been prepared in a volume of 2 l.

Test Run VIII—Test Results Table 15:

| Test Species and Initial Inoculum Level (CFU/g) | Solution 3E CFU per g after: | | Solution 3F CFU per g after: | | Solution 3G CFU per g after: | |
|---|---|---|---|---|---|---|
| | 14 days | 28 days | 14 days | 28 days | 14 days | 28 days |
| P: NCTC 12924 $2.2 \times 10^6$ | <10 | <10 | <10 | <10 | <10 | <10 |
| E: NCTC 12923 $2.0 \times 10^6$ | <10 | <10 | <10 | <10 | <10 | <10 |
| S: NCTC 10788 $1.0 \times 10^6$ | $1.0 \times 10^2$ | <10 | <10 | <10 | <10 | <10 |
| C: NCPF 3179 $2.8 \times 10^6$ | $1.1 \times 10^3$ | 30 | $1.5 \times 10^3$ | 30 | $4.0 \times 10^3$ | 10 |
| A: NCPF 2275 $3.5 \times 10^6$ | $5.0 \times 10^5$ | $9.0 \times 10^4$ | $1.4 \times 10^5$ | $6.0 \times 10^4$ | $1.2 \times 10^5$ | $8.0 \times 10^4$ |

The 3A, 3B and 3C solutions did not achieve the required log reduction for mould (*A. niger*) at the 0.1, 0.15 and 0.2% levels of preservative. Solution 3D, with the 0.25% level of preservative, achieved the required log reduction against all test species. Accordingly, solution 3D was found to be suitable for pharmaceutical use.

Example 4

Solutions of the Invention

Solutions 4A to 4B were prepared. The solutions contained the components shown in Table 16.

TABLE 16

Composition of solutions

| Component | 4A Quantity/g | 4B Quantity/g |
|---|---|---|
| PEG 3350 | 262.500 | 262.500 |
| Sodium Chloride | 7.014 | 7.014 |
| Potassium Chloride | 0.932 | 0.932 |
| Sodium Bicarbonate | 3.570 | 3.570 |
| Acesulfame K | 0.200 | 0.200 |
| Sucralose | 0.060 | 0.060 |
| Blend of methyl paraben (18%), ethyl paraben (9%) and benzyl alcohol (73%) | 1.250 | 1.750 |
| Orange Juice Flavour | 1.600 | None |
| Tropical Fruit Flavour | None | 1.600 |
| Water | To 500 ml | To 500 ml |

Solutions with the components of 4A and 4B shown in Table 16 achieved the required log reduction against all test species (*Pseudomonas aeruginosa, Escherichia coli, Staphylococcus aureus, Candida albicans,* and *Aspergilus niger*) as required by the European Pharmacopoeia as described above. Accordingly, solutions 4A and 4B are found to be suitable for oral pharmaceutical use.

Example 5

Container Containing a Solution of the Invention

Bottle 5a: A 500 ml polyethylene terephthalate (PET) bottle contains 500 ml of solution 4A described in Example 4 above. The bottle is provided with a re-closable closure, and a cap that fits over and grips onto the closure. The cap is suitable for measuring a 25 ml unit treatment volume. The bottle is provided in a carton with instructions for use. The instructions include the instruction that 25 ml of the solution should be measured out and diluted with 100 ml water to make a 125 ml treatment dose.

In analogous bottles, Bottle 5b, contains 500 ml of solution 4B described in Example 4 above; Bottle 5c is a 250 ml polyethylene terephthalate (PET) bottle containing 250 ml of solution 4A; and Bottle 5d is a 250 ml polyethylene terephthalate (PET) bottle containing 250 ml of solution 4B described in Example 4 above.

Bottles 5e, 5f, 5g and 5h are the same as bottles 5a, 5b, 5c and 5d respectively, but with a cap that is suitable for measuring a 12.5 ml unit treatment volume, and instructions that include instruction that 12.5 ml of the solution should be measured out and diluted with 50 ml water to make a 62.5 ml treatment dose.

The invention claimed is:

1. A solution in water comprising the following components at the following concentrations:
    (a) N×(70 to 130) g/L polyethylene glycol (PEG) having an average molecular weight of 2500 to 4500;
    (b) N×(1.6 to 4.0) g/L sodium chloride;
    (c) N×(0.2 to 0.6) g/L potassium chloride;
    (d) N×(0.6 to 2.2) g/L sodium bicarbonate; and
    (e) a preservative comprising methyl paraben, ethyl paraben and benzyl alcohol;
   where N is in the range of 2 to 8.

2. A solution as claimed in claim 1, wherein the solution further comprises:
    (f) flavouring.

3. A solution as claimed in claim 1, wherein the solution further comprises:
    (g) sweetener.

4. A solution as claimed in claim 1, wherein the solution comprises N×(0.3 to 1.4) g/L of the preservative.

5. A solution as claimed in claim 1 further comprising N×(0.02 to 0.2) g/L of sweetener, and/or N×(0.2 to 2) g/L of flavouring.

6. A solution as claimed in claim 5, wherein the sweetener comprises is present and comprises one or both of acesulfame K and sucralose.

7. A solution as claimed in claim 5, wherein the flavouring is present and is Orange Juice or Tropical Fruit flavour.

8. A solution as claimed in claim 1 comprising the following components at the following concentrations:
    (a) 350 to 600 g/L PEG having an average molecular weight of 2500 to 4500;
    (b) 8.0 to 20 g/L sodium chloride;
    (c) 1.0 to 3.0 g/L potassium chloride;
    (d) 3.0 to 11 g/L sodium bicarbonate;
    (e) preservative comprising methyl paraben, ethyl paraben and benzyl alcohol;
    (f) optional flavouring; and
    (g) optional sweetener.

9. A solution as claimed in claim 8, wherein the solution comprises 1.5 to 7.0 g/L of preservative.

10. A solution as claimed in claim 8 comprising 0.1 to 1.0 g/L of sweetener, and/or 1.0 to 10 g/L of flavouring.

11. A solution as claimed in claim 10, wherein the sweetener is present and comprises one or both of acesulfame K and sucralose.

12. A solution as claimed in claim 10, wherein the flavouring is present and is Orange Juice or Tropical Fruit flavour.

13. A solution as claimed in claim 1 comprising the following components at the following concentrations:
    (a) 525 g/L PEG having an average molecular weight of 2500 to 4500;
    (b) 14.028 g/L sodium chloride;
    (c) 1.864 g/L potassium chloride;
    (d) 7.140 g/L sodium bicarbonate;
    (e) preservative comprising methyl paraben, ethyl paraben and benzyl alcohol;
    (f) optional flavouring; and
    (g) optional sweetener.

14. A solution as claimed in claim 13, wherein
    (e) the preservative is present at a level of 2.5 or 3.5 g/L;
    (f) the flavouring is present at a level of 3.2 g/L; and
    (g) the sweetener is present at a level of 0.52 g/L.

15. A solution as claimed in claim 1 that is substantially free from any sulphate component.

16. A solution as claimed in claim 8 that is substantially free from any sulphate component.

17. A method of preparing a concentrate solution as claimed in claim 1 comprising combining the components (a) to (e) with water.

18. A container containing a solution as claimed in claim 1.

19. A container as claimed in claim 18 containing 25 ml, 100 ml, 150 ml, 250 ml or 500 ml of solution.

20. A container as claimed in claim 18 containing:
(a) x×262.50 g PEG 3350;
(b) x×7.014 g sodium chloride;
(c) x×0.932 g potassium chloride;
(d) x×3.570 g sodium bicarbonate;
(e) preservative comprising methyl paraben, ethyl paraben and benzyl alcohol;
(f) optional flavouring;
(g) optional sweetener; and
(h) water to x×500 ml;
wherein x is 0.5 to 2.

21. A container as claimed in claim 20 wherein x is 0.5 or 1.

22. A kit comprising a container as claimed in claim 18 together with instructions for use.

23. A kit as claimed in claim 22, wherein the instructions for use instruct the user to dilute a stated volume of the solution with a stated volume of water.

24. A kit comprising a container as claimed in claim 18 together with a measuring accessory for measuring out a defined volume of the solution.

25. A method of preparing a solution for the treatment of constipation or faecal impaction, which method comprises combining a volume V of solution as claimed in claim 1 with water by the addition of a volume (N−1)×V of water.

26. A solution that has been prepared by combining a volume V of solution as claimed in claim 1 with water by the addition of a volume (N−1)×V of water.

27. A method of treating constipation or faecal impaction, which method comprises administering orally to the subject a solution as claimed in claim 26.

* * * * *